United States Patent
Kim et al.

(10) Patent No.: US 8,822,690 B2
(45) Date of Patent: Sep. 2, 2014

(54) HIGH TRANSMISSIONAL YELLOW DYE FOR LCD AND SYNTHETIC METHOD THEREOF

(71) Applicants: LG Display Co., Ltd., Seoul (KR); Seoul National University R&DB Foundation, Seoul (KR)

(72) Inventors: YoungHoon Kim, Goyang-si (KR); JiChul Lim, Pyeongtaek-si (KR); ByungGun Ahn, Paju-si (KR); SangHun Han, Gunpo-si (KR); JaePil Kim, Seoul (KR); SeHun Kim, Seoul (KR); Jun Choi, Seoul (KR); JinWoong Namgoong, Seoul (KR)

(73) Assignee: LG Display Co., Ltd., Seoul (KR)

( * ) Notice: Subject to any disclaimer, the term of this patent is extended or adjusted under 35 U.S.C. 154(b) by 56 days.

(21) Appl. No.: 13/731,593

(22) Filed: Dec. 31, 2012

(65) Prior Publication Data

US 2014/0073794 A1  Mar. 13, 2014

(30) Foreign Application Priority Data

Sep. 10, 2012 (KR) .......................... 10-2012-0100060

(51) Int. Cl.
*C07D 403/14* (2006.01)
*C07D 209/64* (2006.01)
*C07D 401/10* (2006.01)

(52) U.S. Cl.
CPC ............ *C07D 403/14* (2013.01); *C07D 209/64* (2013.01); *C07D 401/10* (2013.01)
USPC ........................................................ 546/167

(58) Field of Classification Search
CPC .. C07D 403/14; C07D 209/64; C07D 251/54; C07D 401/10
USPC ........................................................ 546/167
See application file for complete search history.

(56) References Cited

U.S. PATENT DOCUMENTS

2012/0287524 A1* 11/2012 Uhm et al. .................... 359/891

FOREIGN PATENT DOCUMENTS

JP  2001-335711  * 4/2001

* cited by examiner

*Primary Examiner* — D M Seaman
(74) *Attorney, Agent, or Firm* — Birch, Stewart, Kolasch & Birch, LLP

(57) ABSTRACT

The present invention relates to high transmission yellow dye for LCD, dye dispersion comprising the dye, coloring composite comprising the dye dispersion, color filter comprising the coloring composite, and synthetic method thereof.

16 Claims, 41 Drawing Sheets

| Dyes | $\lambda_{max}$(nm) | $\varepsilon$ (L mol$^{-1}$ cm$^{-1}$) |
|---|---|---|
| QP1 | 426;452 | 25,490 |
| QP2 | 412;430 | 17,479 |
| QP3 | 430;456 | 34,872 |
| QP4 | 428;452 | 33,545 |

1. PR Formulation:
- Solid Contents: 20 %
- Colorant Contents: 1.0 %
    2 yellow (QP3, QP4), 6 green (GD4, GD5, GD5', GD6, GD11, GD12)
- Binder, Additives (addhesiveness/surfactant)
- MM, PI: none
- Solvent: PGMEA only

2. Spin coating: 350rpm on 5×5 bare glass

3. Prebake: contact 90℃ / 100s
4. Exposure: None
5. Development: None
6. Postbake: for 20min @ 180/200/230℃
7. Absorption Spectra: UV-vis. spectrophotometer

HIGH TRANSMISSIONAL YELLOW DYE FOR LCD AND SYNTHETIC METHOD THEREOF

RELATED APPLICATION

This application claims the benefit of priority to Korean Patent Application No. 10-2012-0100060, filed on Sep. 10, 2012, which is hereby incorporated by reference for all purposes as if fully set forth herein.

BACKGROUND OF THE INVENTION

1. Field of the Invention

The present invention relates to high transmission yellow dye for LCD, dye dispersion comprising the dye, coloring composite comprising the dye dispersion, color filter comprising the coloring composite, and synthetic method thereof.

2. Background of the Invention

A color filter used in Liquid Crystal Display (LCD) is used for materialize color images in the Display, which can be prepared through a process consisting of coating pigments on a basic circuit board with various methods, and curing and patterning them. The color filter is one that each of 3 color pixel parts is formed on a transparent circuit board as like a glass. The color filter used in a display device or a solid state image sensor usually has a coloring pattern of the three primary colors comprising Red®, green (G) and Blue (B) and play a role in coloring a light passing through or segregating it to the 3 primary colors. Dyes displaying red, green, and blue consist of fine particles, namely pigments, and these pigments display each of red, green, and blue color by mixing dyes representing similar colors rather than being used independently to obtain a color display property in a desired range.

Recently, technology development of LDC toward larger screen and higher definition has been advanced and its usage has been expanded sharply from a display for laptop computer to a monitor for a desktop computer and television monitor. In these situations, the color filter used in LCD is required to have high color purity. Especially in high definition display making high definition image display possible, it becomes important to satisfy this requirement. A light passing through a color filter is to be colored with the color of each pixel and colors of the lights are synthesized to form a color image. Therefore, a color filter having very high purity pixel is required as certain 3 colors of RGB making it possible.

Besides due to propagation of digital camera and camera equipped mobile phone, demand of solid state image sensors such as CCD image sensor has increased remarkably also. As the color filter is used as a key device of these displays or optical elements, demand on cost reduction as well as demand on high definition of the color filter increases.

Dyes used in the color filter are required to have following properties. Having a desirable light absorption property in color reproduction; having no development of optical faults such as light scattering or color non-uniformity of solid state image sensor causing contrast lowering of LCD or optical density non-uniformity causing coarse sensation; having proper resisting properties such as thermal resistance, light resistance, and damp heat resistance; and being capable of preparation of thin film.

Demands on LCD with high definition, namely improved contrast and color purity increase and it is required for improvement of contrast that the particle size of dyes (organic pigments) in photosensitive resin composition for formation of color filter is further smaller. In addition, it is important also to increase content of dyes (such as organic pigments) against solids of the photosensitive resin composition for improvement of color purity. Besides, in the recent color filter for solid state image sensors such as CCD, high definition is required further. Therefore, miniaturization of dye is desired to inhibit color non-uniformity by coarse particles of the dye.

The dye or the pigment used coloring matter is required to contain following properties: Having a desirable absorption property in color reproduction; and having good fastness property in its application environment including light resistance, thermal resistance, and resistance to oxidative gas such as ozone. Additionally, when the dye is a pigment, it is substantially insoluble in water or organic solvent and it is necessary to contain following properties: having good fastness resisting chemical; and giving no damage to desirable absorption properties in molecular dispersion even in being used as particles. The requirements may be controlled with strength and weakness of intermolecular interaction and it is difficult to make both of them compatible because they are in trade off relationship.

Under these situations, a technology using a dye instead of a pigment has been suggested. When using a dye instead of a pigment, accomplishment of high resolution is expected by solving problems such as color non-uniformity and coarse sensation in the color filter for solid state image sensor and improvement of optical properties such as contrast or haze is expected in LCD or Organic Light-Emitting Display (OLED).

However, coloring curable composition containing dyes has following problems also:

(1) The dyes in molecular dispersion state have insufficient light resistance and thermal resistance generally compared with the pigments forming molecular aggregates; especially, when forming ITO (Indium tin oxide) film used widely as an electrode of LCD, there is a problem that optical properties are changed by high temperature process.

(2) The dyes in molecular dispersion state have insufficient solvent resistance generally compared with the pigments forming molecular aggregates;

(3) As the pigment tends to inhibit radical polymerization reaction, there are some difficulties in designing coloring curable composition in a system using the radical polymerization as a mean of curing.

(4) Conventional dyes have lower solubility in alkali aqueous solution or organic solvent, so it is difficult to obtain a coloring curable composition having a desired spectrum;

(5) The dyes are likely to interact with other ingredients in the coloring curable composition, so it is difficult to control solubility of exposure and non-exposure part (developing property);

(6) When molar extinction coefficient of the dye ($\epsilon$) is low, it is needed to add large amount of the dye. Thus, it is required to reduce the amount of other ingredients such as polymeric chemical (monomer), binder, or photo-initiator in the coloring curable composition relatively, curing property, heat resistance after curing, and developing property of the composition are lowered.

Currently, metal halide phthalocyanine dye or metal halide phthalocyanine pigment is used generally for forming green pixel.

However the transmission spectrum of phthalocyanine series dye as a main green dye has similar transmission spectrum to that required in the color filter, but its absorption in shorter wavelength zone is insufficient. Therefore, when it absorbs the shorter wavelength zone further completely, it is possible to expect higher color reproduction range that current one theoretically.

Therefore, it is required to develop a compensation dye that not only can overcome the above mentioned disadvantages but also absorb the shorter wavelength zone effectively, for instance an improved dye for color filter of LCD able to be used as a compensation dye for green dye.

SUMMARY OF THE INVENTION

An object of the present invention is to provide high transmission yellow dye for LCD, dye dispersion comprising the dye, coloring composition comprising the dye dispersion, color filter comprising the coloring composition, and synthetic method thereof.

In the present invention, it was intended to develop hybrid color photo resist (PR) proper to low electric power LED BLU light source substituting for CCFL, a conventional LCD color filter backlight (BLU) light source. For this, it is necessary to develop a high durability yellow compensation dye able to absorb short wavelength in the range of 400~500 nm as a compensation dye for the main green dye and it is intended to materialize transmission spectrum for optimal green color filter by mixing the high transmission green dye and the yellow dye appropriately.

An example of the present invention to accomplish the objective comprises a dye of Formula 1:

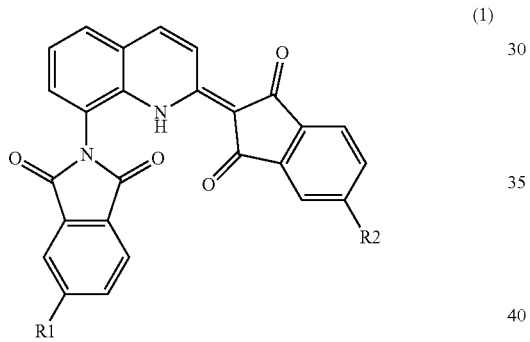

(1)

wherein, the R1 or R2 is one selected from a group consisting of hydrogen, halogen, unsubstituted or substituted alkyl, and unsubstituted or substituted aryl independently.

The transmission spectrum of phthalocyanine series green dye has similar transmission spectrum to that required in the color filter, but its absorption in shorter wavelength zone does not occur adequately. Accordingly a compensation dye to compensate the transmission spectrum by absorbing the shorter wavelength zone further completely comes to be needed. It is possible to increase color reproduction range by using a compensation dye and for this, yellow compensation dye with good durability, which can absorb the wavelength range below 480 nm effectively, is needed. However, general dyes and pigments representing yellow absorb higher energy in the shorter wavelength range than other color, so show lower thermal and light resistance. In order to solve this problem, the present invention provides a quinophthalone series yellow compensation dye satisfying high thermal resistance and light resistance and a yellow dye able to absorb shorter wavelength range effectively by diversifying their structure.

Quinophthalone is a yellow dye having maximum absorption wavelength in 400~470 nm range, which shows properties such as good thermal resistance and very sharp absorption spectrum. Basic structure of the quinophthalone dye consists of quinoline part and anhydrous phthalic part. In the present invention, it was intended to introduce 2 anhydrous phthalic structures to the quinoline in order to improve thermal resistance by increasing molecular weight, maintain the sharp spectrum of quinophthalone and introduce halogen element to the anhydrous part to attempt additional improvement of light resistance. Synthesis design of the quinophthalone series yellow compensation dye according to the present invention is as follows.

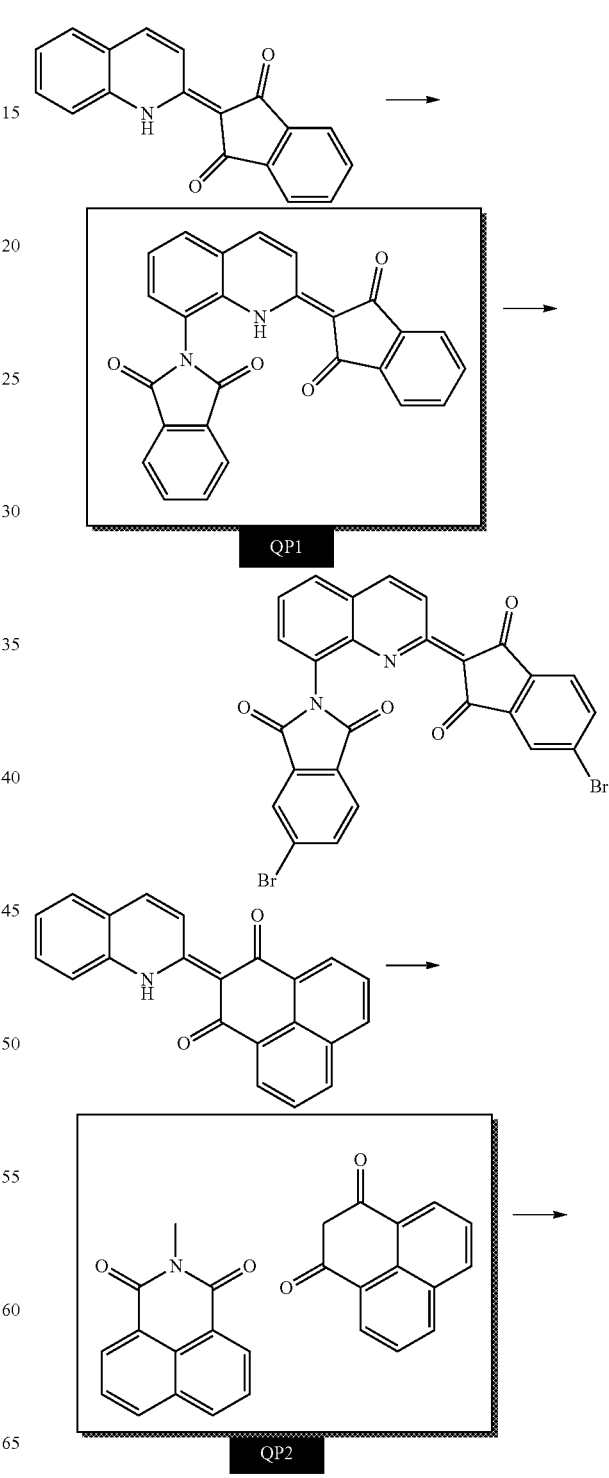

-continued

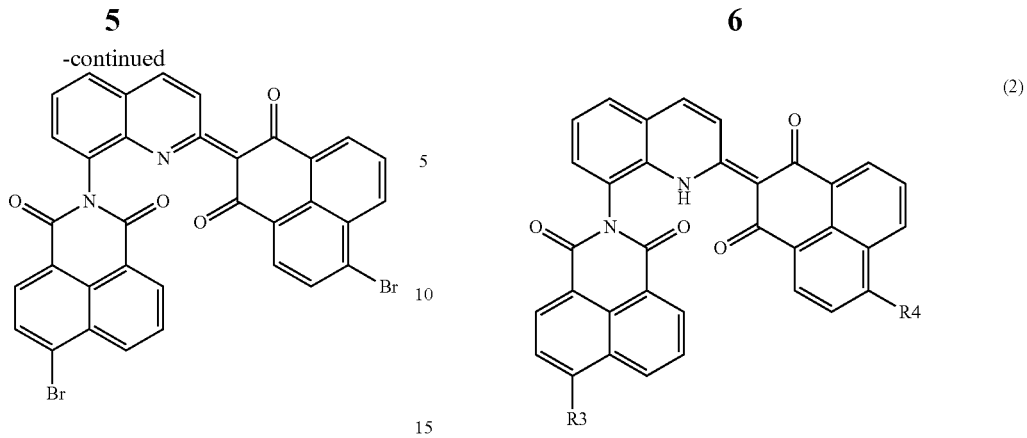

As an example of the present invention, the dye of Formula 1 may be further improved to have a physical property proper to a photo resist for LCD. A mimetic diagram of structural design of the improved quinophthalone series dye according to the present invention is as follows.

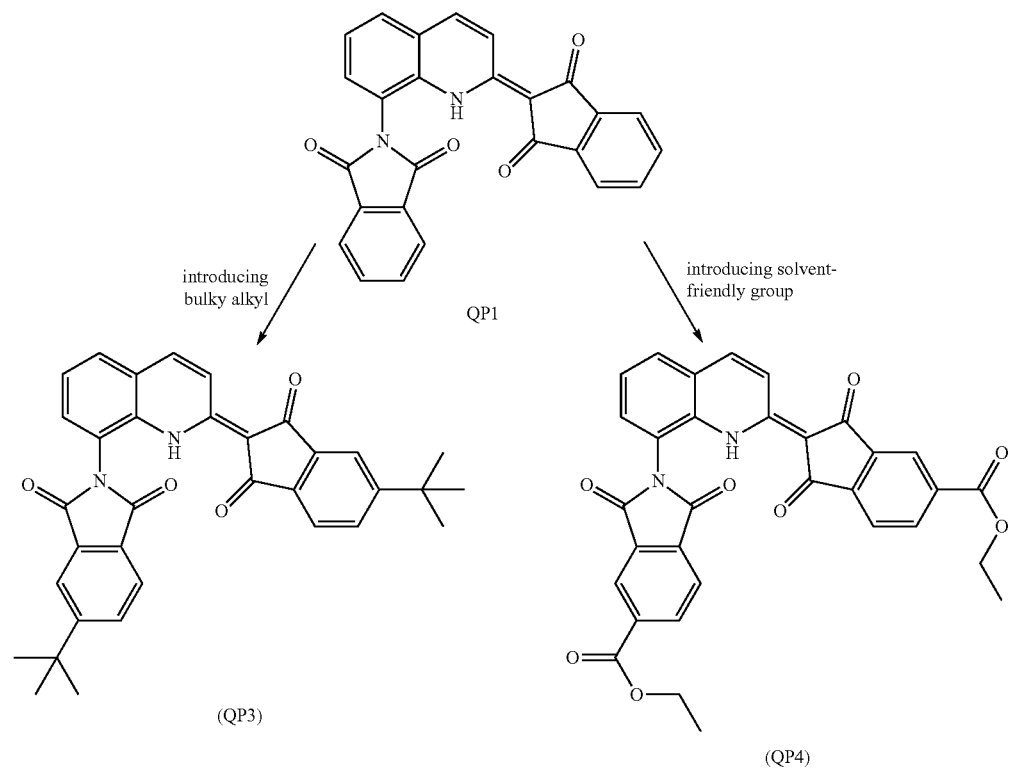

wherein, the R3 or R4 is one selected from a group consisting of hydrogen, halogen, unsubstituted or substituted alkyl, and unsubstituted or substituted aryl independently. Synthesis New design is to attempt improvement for increasing solubility. It was attempted to prevent aggregation by introducing bulk-sized alkyl residue to the basic structure and in order to give it affinity to the process solvent, PGMEA, solvent-friendly functional group introduced structure was designed.

Accordingly, the R1 or R2 may be selected from a group consisting of halogen, bulk-sized alkyl residue and solvent friendly substituent according to solvents used in dissolution of the dye independently.

Preferably, the R1 or R2 may be selected from a group consisting of halogen, tert-butyl, and carboxylate independently.

Another example of the present invention to accomplish the objective comprises a dye of Formula 2:

design of the quinophthalone series yellow compensation dye of Formula 2 is illustrated in the above mentioned mimetic diagram.

As another example of the present invention, the dye of Formula 2 also may be further improved to have a physical property proper to a photo resist for LCD.

In order to improve solubility, aggregation may be prevented by introducing bulk-sized alkyl residue to the basic structure and in order to give it affinity to the process solvent, PGMEA, solvent-friendly functional group may be introduced.

Accordingly, the R3 or R4 may be selected from a group consisting of halogen, bulk-sized alkyl residue and solvent friendly substituent according to solvents used in dissolution of the dye.

Preferably, the R3 or R4 may be selected from a group consisting of halogen, tert-butyl, and carboxylate independently.

The dye of Formula 1 and Formula 2 may be a dye absorbing 400 nm~500 nm of wavelength range.

Preferably, the dye of Formula 1 and Formula 2 may be one absorbing wavelength range below 480 nm and more preferably, it may be one absorbing 450 nm~480 nm of wavelength range.

The dye of Formula 1 and Formula 2 may be one used as compensation dye for green dye.

Another example of the present invention to achieve the objective comprises a dye dispersion comprising the dye of Formula 1 and Formula 2.

Another example of the present invention to accomplish the objective is a coloring composition comprising the said dye dispersion.

Another example of the present invention to accomplish the objective is a color filter formed by using the said coloring composition.

Another example of the present invention to accomplish the objective comprises a synthetic method of the dye comprising:

(a) a step to form 8-aminoquinaldine by reducing 8-nitroquinaldine;

(b) a step to produce an intermediate by adding at least one chemical selected from a group consisting of

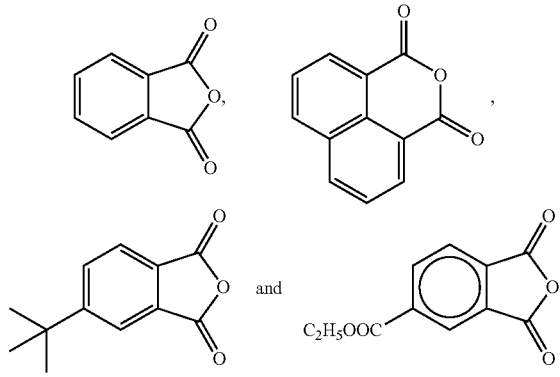

to the 8-aminoquinaldine; and (c) a step to produce a dye by adding at least one chemical selected from a group consisting of

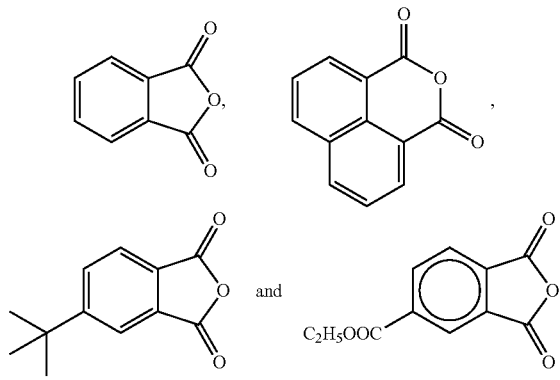

to the intermediate.

The synthetic method of the dye may further comprise a step (d) halogenation after the step (c).

Effects of Invention

The present invention provides a yellow compensation dye with high durability able to absorb the shorter wavelength range by complementing the main pigment dye, in order to provide a green dye to cope with low electric power type LED BLU light source to substitute conventional CCFL BLU. Through color mixing with the green dye, it is possible to provide an optimal green color filter. In addition, the dye synthesized in the present invention has high durability (high heat resistance and high thermal resistance) suitable to present LCD process as well as solubility proper to conventional pigment type solvent (PGMEA). In other words, the present invention provides an optimal synthetic method and mass synthesis technology as well as high transmission yellow dye for LCD.

DETAILED DESCRIPTION OF THE INVENTION

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

1. Synthesis of Dye 1-1. Synthesis of QP1

(1) Reduction

Put 1.88 g (0.01 mol) of 8-nitroquinaldine to 20 ml of ethanol and add 11.27 g (0.05 mol) of $SnCl_2$ slowly, during stirring the mixture under nitrogen gas. Raise the temperature of reaction mixture to 70° C. and circulate it for 30 min. After completion of the reaction, cool the mixture to room temperature and then adjust pH to 7-8 with sodium bicarbonate solution, dropping it to 300 ml of distilled water in a cold water bath slowly. Put the obtained emulsion into a separatory funnel, obtain product by adding 700 ml of ethyl acetate, and wash it with saturated salt water. The product exists in state of being dissolved in the ethyl acetate and water was removed from it by passing it through $MgSO_4$. By evaporating the ethyl acetate, the yellow product, 8-aminoquiniline, was obtained in oil phase and yielded to solid state by storing it in a freezer. Its reaction formula is as follows.

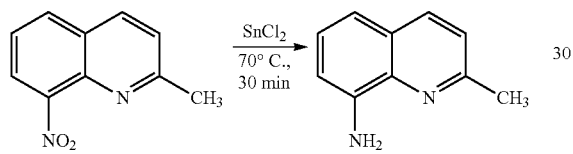

(2) Imidization

After adding 1.48 g (0.01 mol) of anhydrous phthalic and 40 g of trichlorobenzene to 1.58 g (0.01 mol) of 8-aminoquidiline, circulate the mixture at 220° C. for 4 hr. After completion of the reaction, add 1.48 g (0.01 mol) of anhydrous phthalic and 0.45 g (0.003 mol) of $ZnCl_2$ and circulate the mixture for 5 hr. After completion of the reaction, cool to room temperature and add the reactant solution to 1 L of n-hexane slowly to be precipitated. Perform vacuum filtration of the produced solid matter, wash it with 1% sodium hydroxide solution, and dry it in a vacuum oven for 1 day. Dissolve the obtained dye in chloroform, perform vacuum filtration of it, and evaporate remaining solution to remove the solvent. And it was purified through column chromatography using EA:hexane=1.25:1. Its imidization reaction formula is as follows.

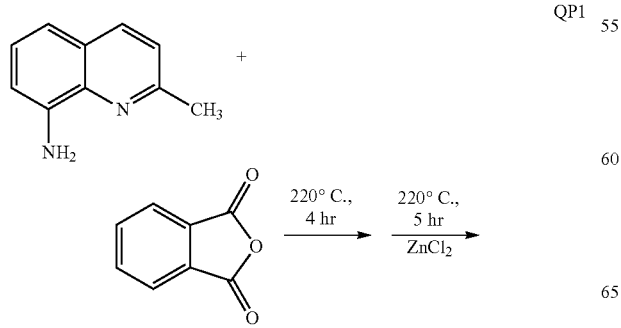

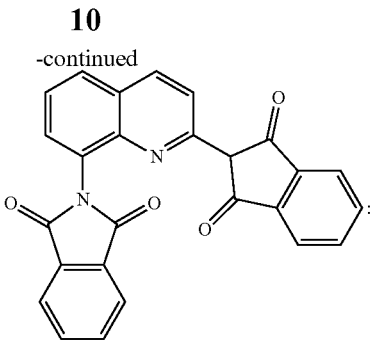

1-2. Synthesis of QP2~QP4

Excluding using

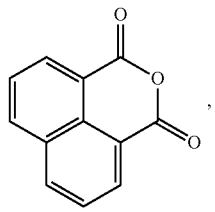 (QP2)

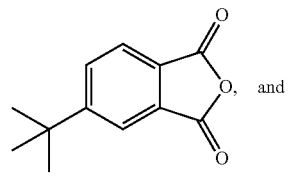 (QP3) and

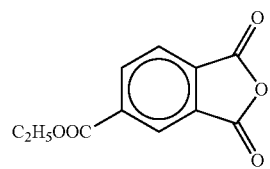 (QP4)

respective instead of

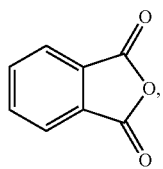 [SMILES: O=C1OC(=O)c2ccccc21]

QP2~QP4 was synthesized with same method and same molar equivalent to the synthesis of the said 1-1.QP1.

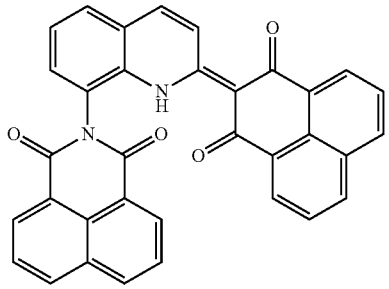

QP3

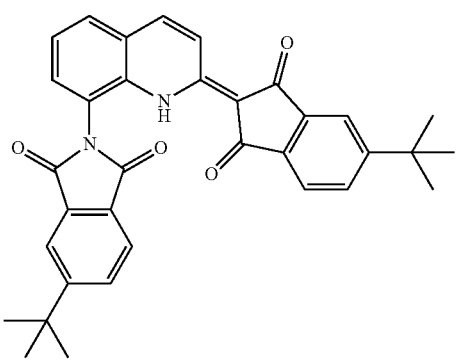

QP4

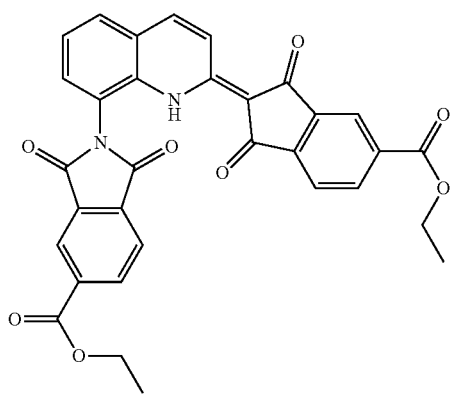

2. Spectroscopic Analysis of Dye

Figure 1:
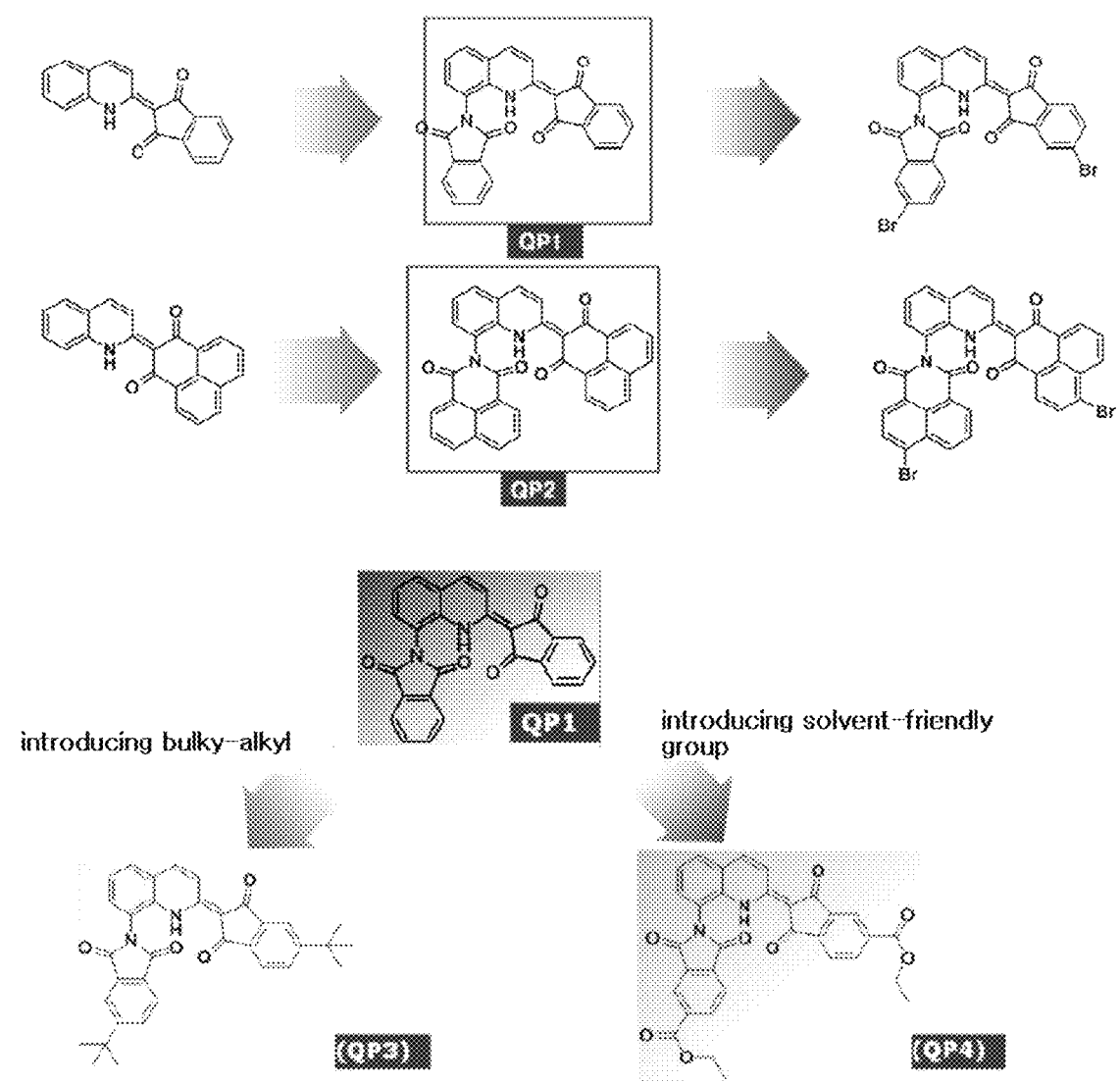
FIG. 1 shows a mimetic diagram of the quinophthalone series dye according to the present invention.
Figure 2:
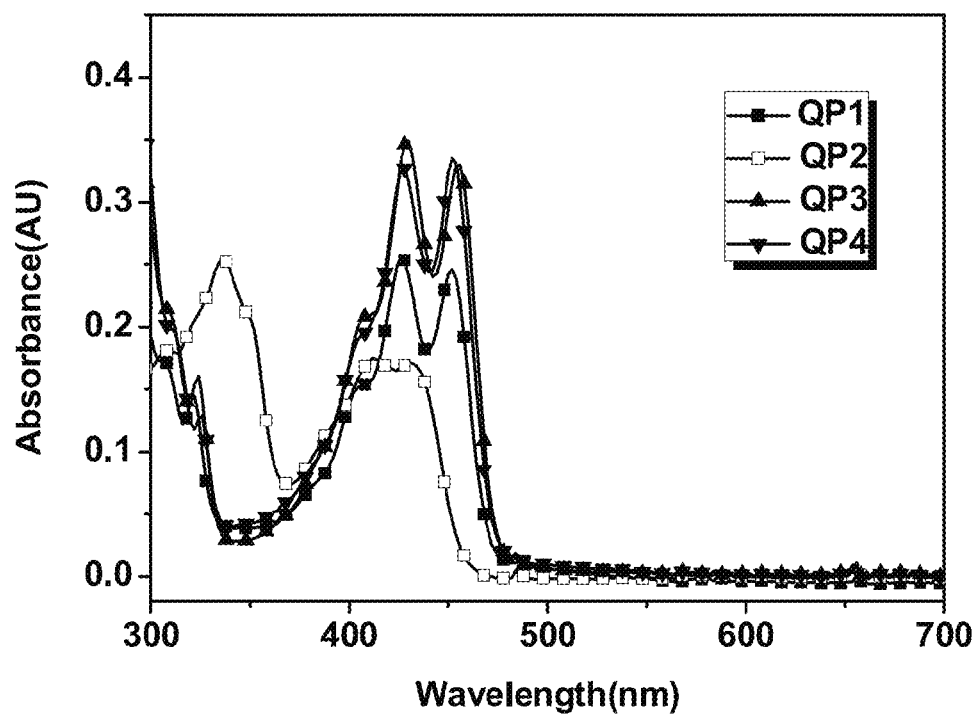
FIG. 2 shows a graph and a table displaying UV-VIS absorption spectrum peaks of the synthesized dyes.

FIG. 2 shows UV-vis absorption peaks of the synthesized quinophthalone series dyes. As shown in the graph, it was found that excellent solubility of QP3 and QP4 would be linked to excellent color property. As QP3 and QP4 increased the molar extinction coefficient further in addition to somewhat bathochromic-shift of λmax, they show very strong and sharp absorption peaks prior to 500 nm. This is very ideal absorption peak for being used as a yellow compensation dye to correct the major green dye. It was found that among them, as QP3 had the sharpest slope of absorption reduction just prior to 500 nm and its absorption after 500 nm was the lowest, it showed the most excellent color property.

3. Thermal Resistance Analysis of Dye

Figure 3:
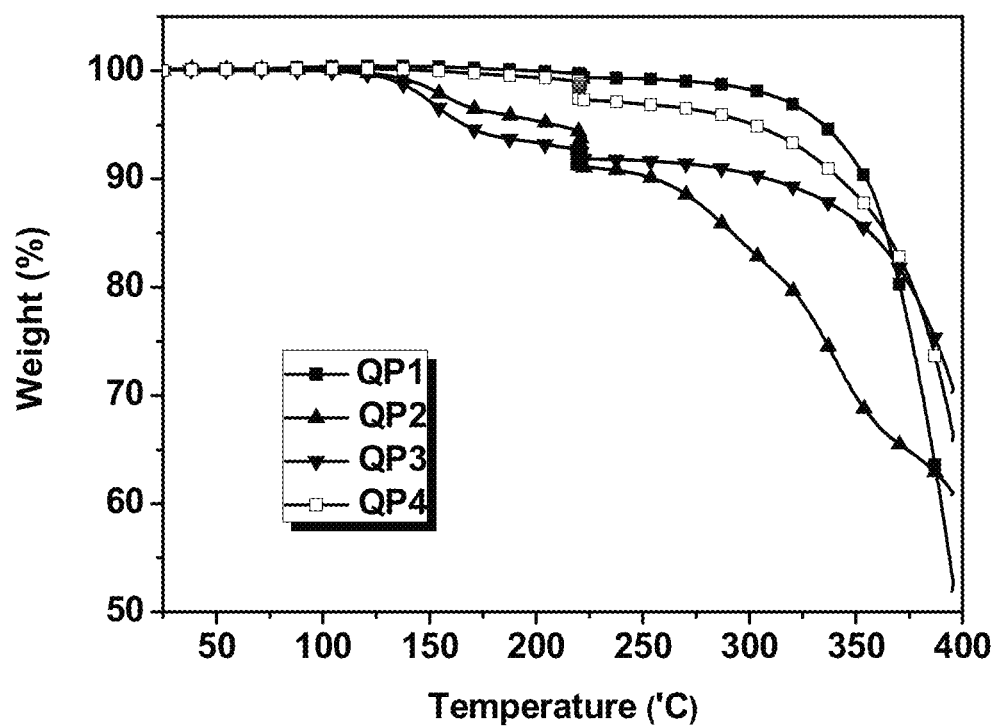
FIG. 3 is a TGA (Thermogravimetric Analyzer) graph of the synthesized dyes.

Through Thermo Gravimetric Analyzer (TGA), Thermogravimetric Analyzer 2050 (TA instruments), thermal resistance of the synthesized dye was measured (FIG. 3). For the thermal resistance test, change of mass reduction rate (w %) was measured by passing through isothermal section at 220° C. for 30 min, raising the temperature to 30° C.~400° C. in 10° C./min. In order to apply it as a dye material for LCD color filter, the mass reduction in isothermal zone must be less than 5%. As shown in the graph, it was found that the mass reduction in isothermal zone increased in order of QP1<QP3<QP4<QP2. In case of QP3 and QP4, it was analyzed that functional groups introduced to improve the solubility gave somewhat reciprocal effects to the thermal resistance of dye. However, as the weight loss was less than 5% in the isothermal zone, it was found to show appropriate level to applying to the color filter. It was found that QP3 had weight loss in relative low temperature zone below 200° C. It seems that the weight loss is caused by effects of solvents or impurities rather than thermal resistance of dye itself. This might be confirmed from the results that in the high temperature zone over 300° C. the weight loss of QP3 was saturated and the best thermal resistance property was shown.

4. Solubility Analysis of Dye

In below Table 1, there were qualitative solubility assessment results of the synthesized quinophthalone series dye. As shown in the Table 1, it was found that the solubility order in both common organic solvent and process solvent, PGMEA, was roughly QP4=QP3>QP1>QP2. This means that new design to improve solubility is successful. It was shown that QP3 improving intermolecular steric hindrance by bulk-sized alkyl residue and QP4 increasing affinity to the process solvent, PGMEA, by introducing carboxylate functional group increased its solubility successfully than QP1. This shows a possibility to be linked to improvement of optical property through lowering of light scattering by reducing particle size of dye molecule in solution phase.

TABLE 1

|  | QP1 | QP2 | QP3 | QP4 |
|---|---|---|---|---|
| $CH_2Cl_2$ | ++ | + | +++ | +++ |
| PGMEA | ++ | + | +++ | +++ |

Figure 15:
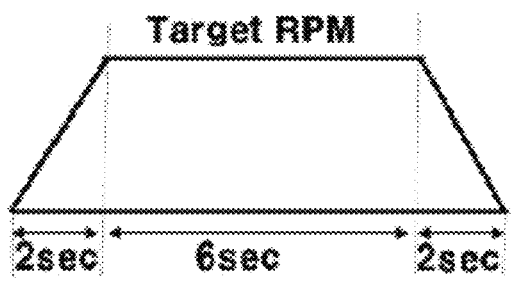
FIG. 15 is showing the condition under which the color filter application property assessment for QP3 and QP4 is performed.

+++: >5.0 * $10^4$ mg liter$^{-1}$
++: >5.0 * $10^3$ mg liter$^{-1}$
+: >5.0 * $10^2$ mg liter$^{-1}$ 5. Color Filter Application Property Assessment
Primary Property Assessment of QP3 and QP4
Color simulation was performed according to the condition described in FIG. 15.

Figure 4A:
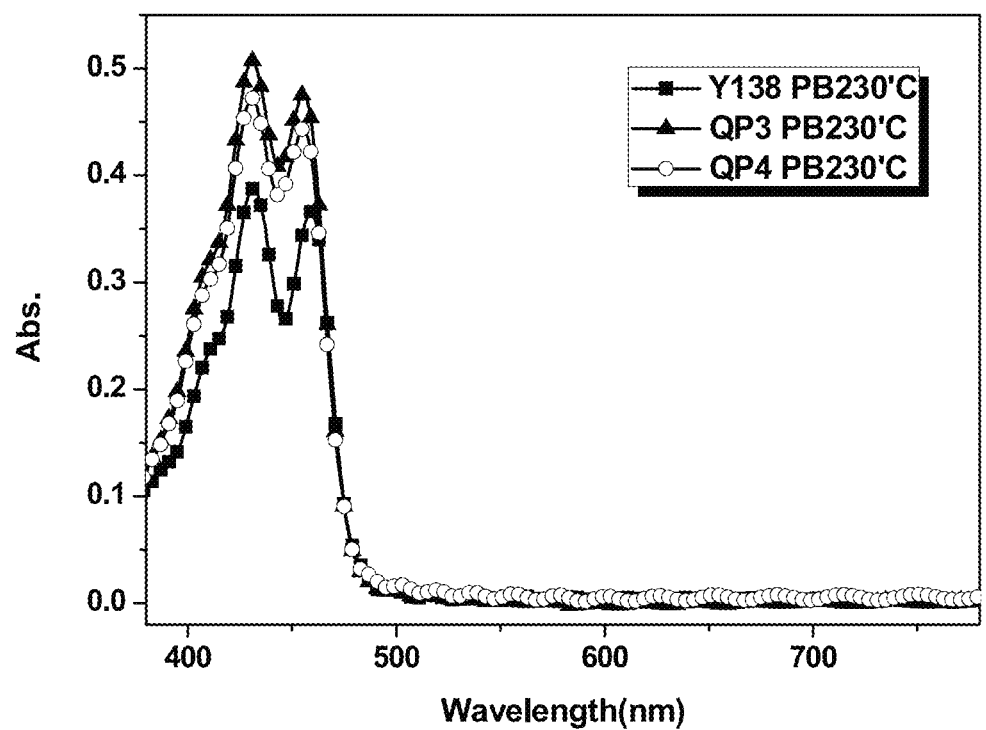
FIGS. 4A-4C show absorption spectrums by temperatures of the dye QP3 and QP4.
Figure 4B:
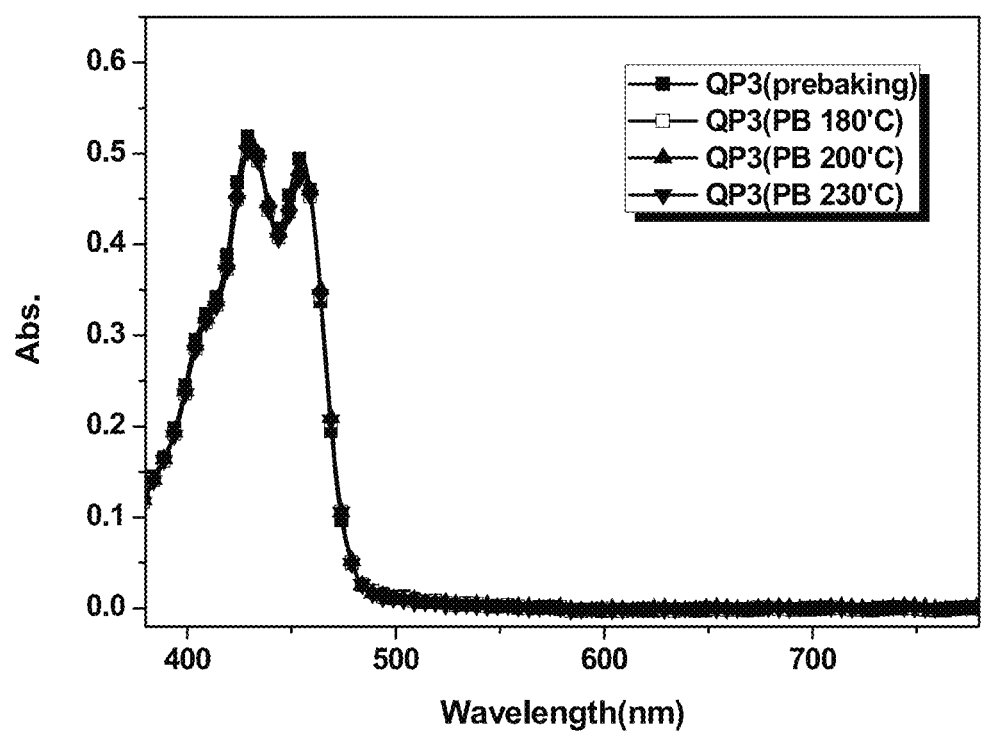
Figure 4C:
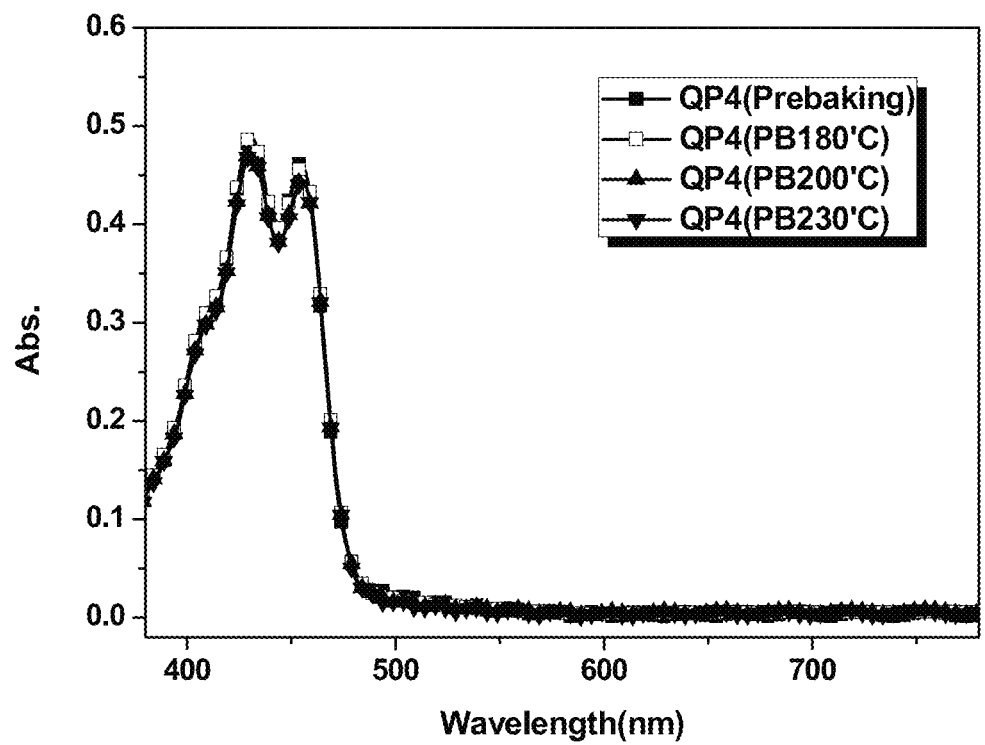

It was considered that both the thermal resistance on the spectrum of QP3 and QP4 were excellent (FIGS. 4A-4C). This was stated in figures through independent thermal resistance assessment of PR (photo resist) later. It was found that both dyes had similar spectrum, but transmittance of QP4 might be somewhat lowered compared with QP3 because its absorption increased relatively after 480 nm. As the molar extinction coefficient was formed to be somewhat higher, merits of the dye were exposed. All the 1% solubility of dye to PGMEA was in satisfactory level and particularly, QP3 was dissolved immediately after addition.

Figure 5A:
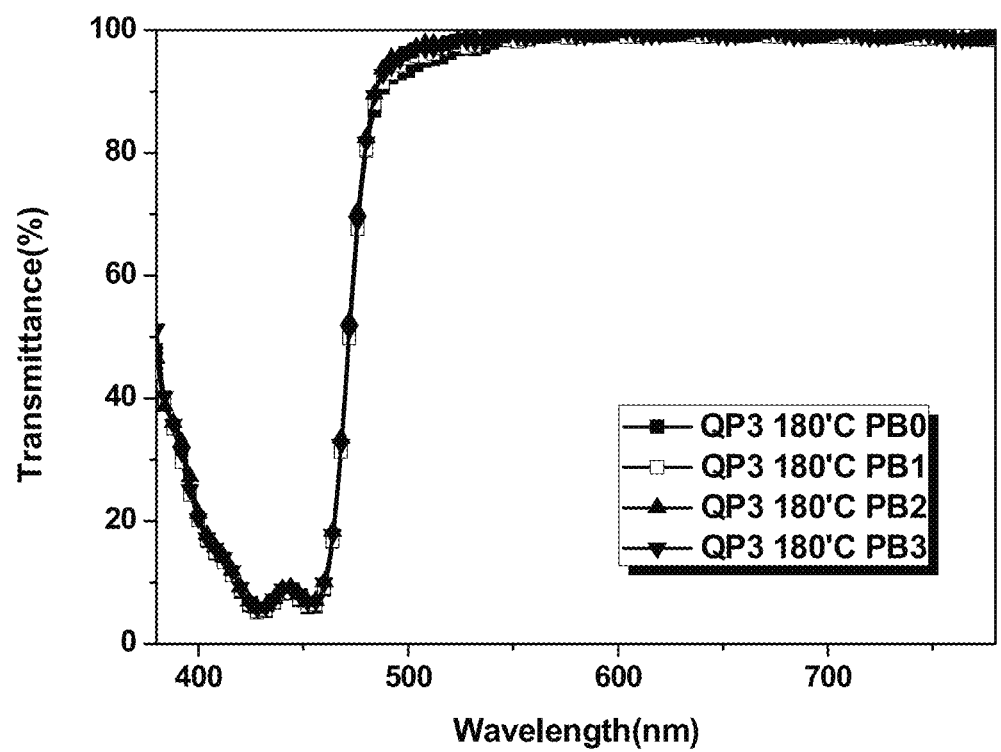
FIGS. 5A-5C are transmission spectrum graphs by number of PB of QP3.
Figure 5B:
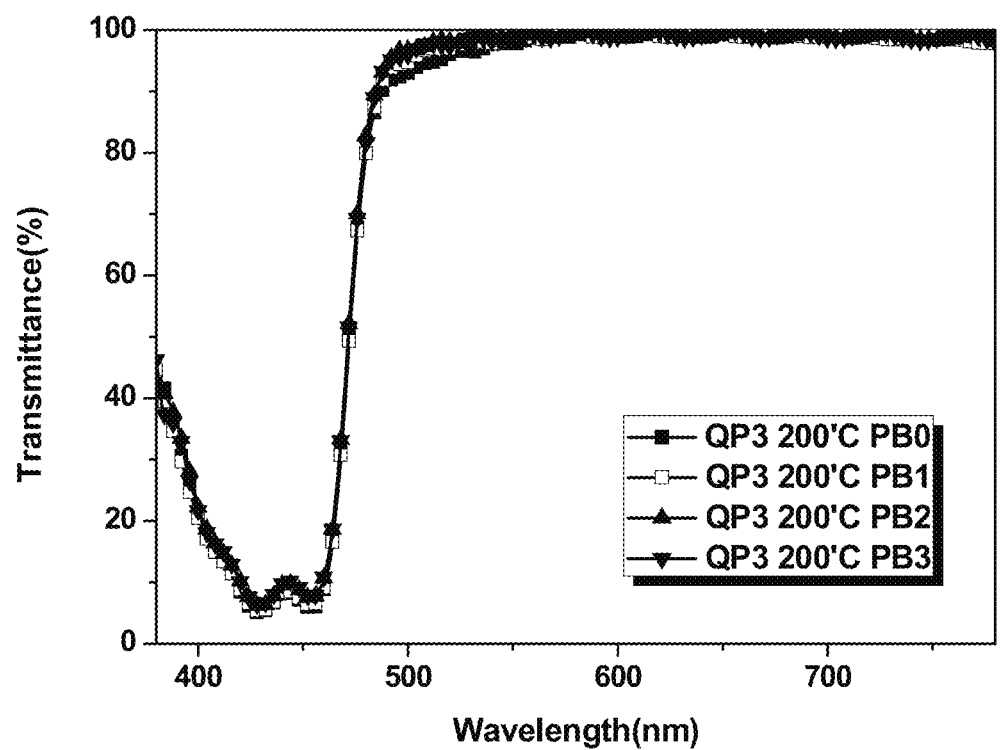
Figure 5C:
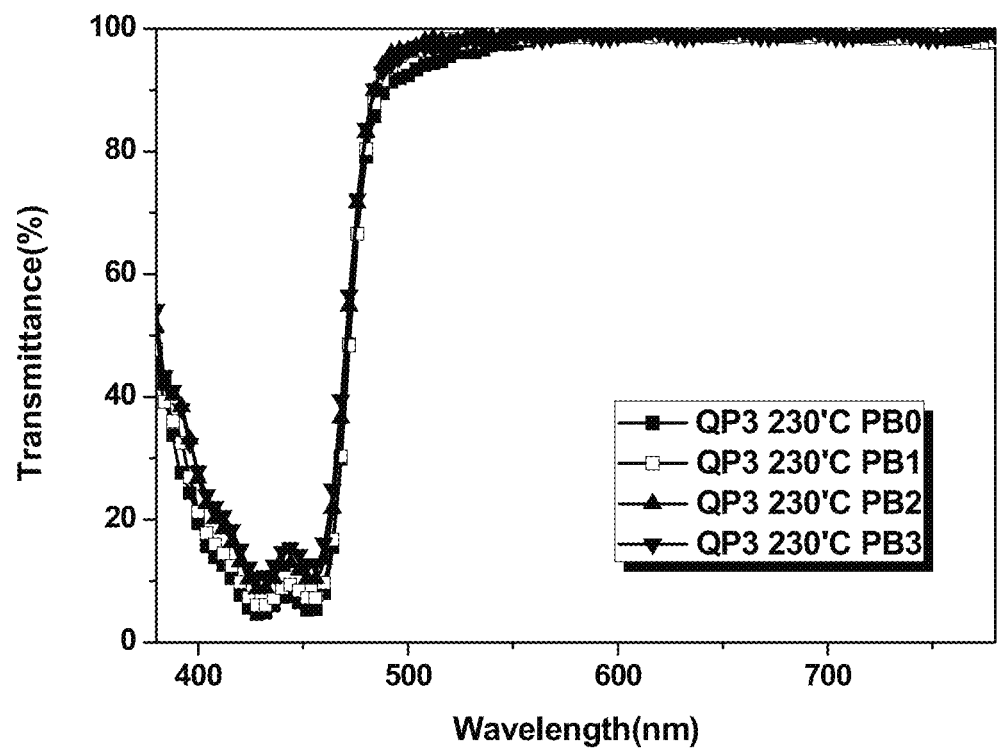
Figure 6A:
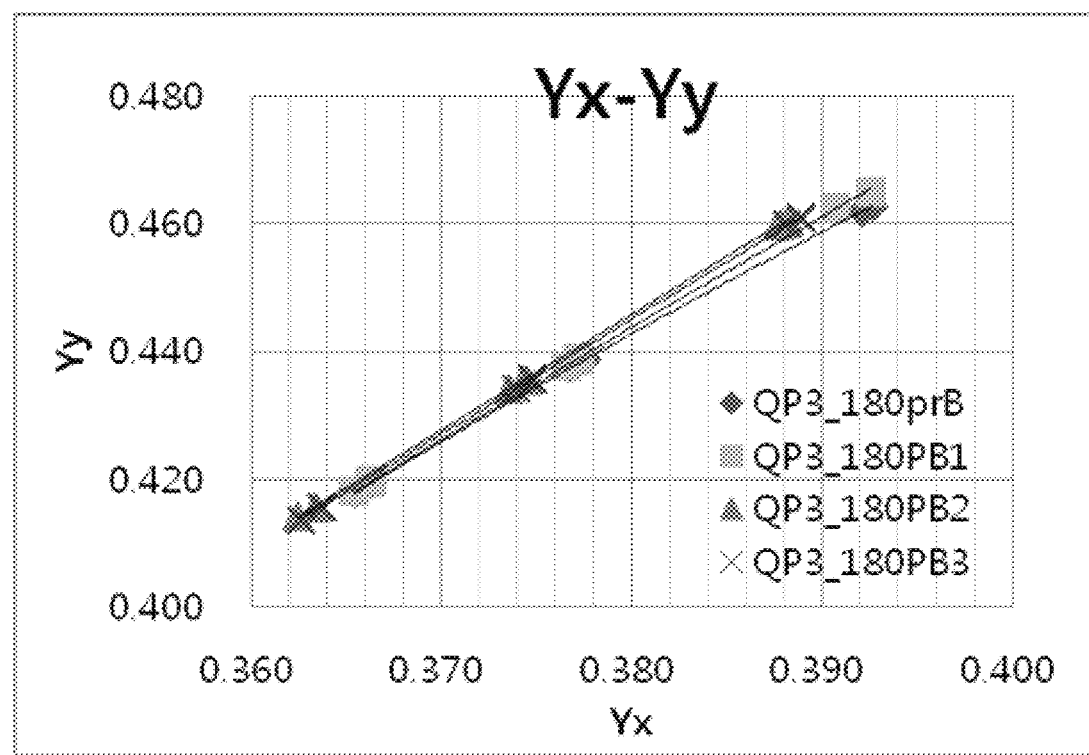
FIGS. 6A-6F are graphs showing color coordinate value change by temperatures of QP3.
Figure 6B:
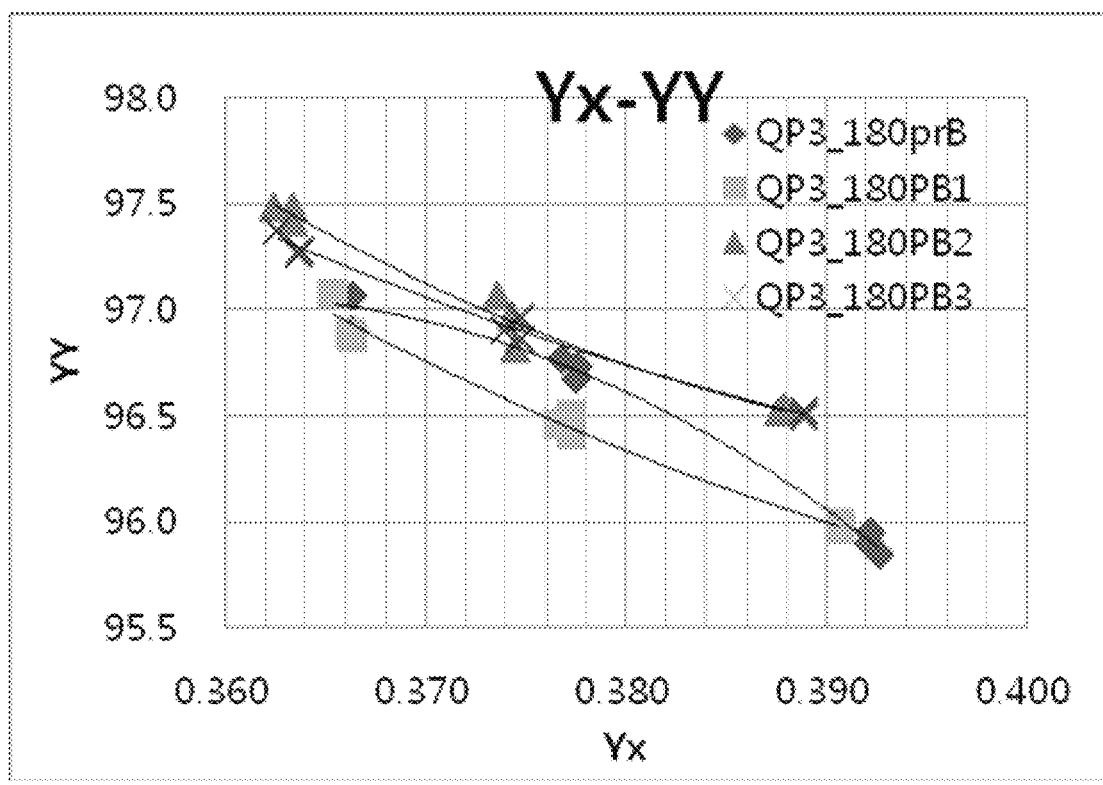
Figure 6C:
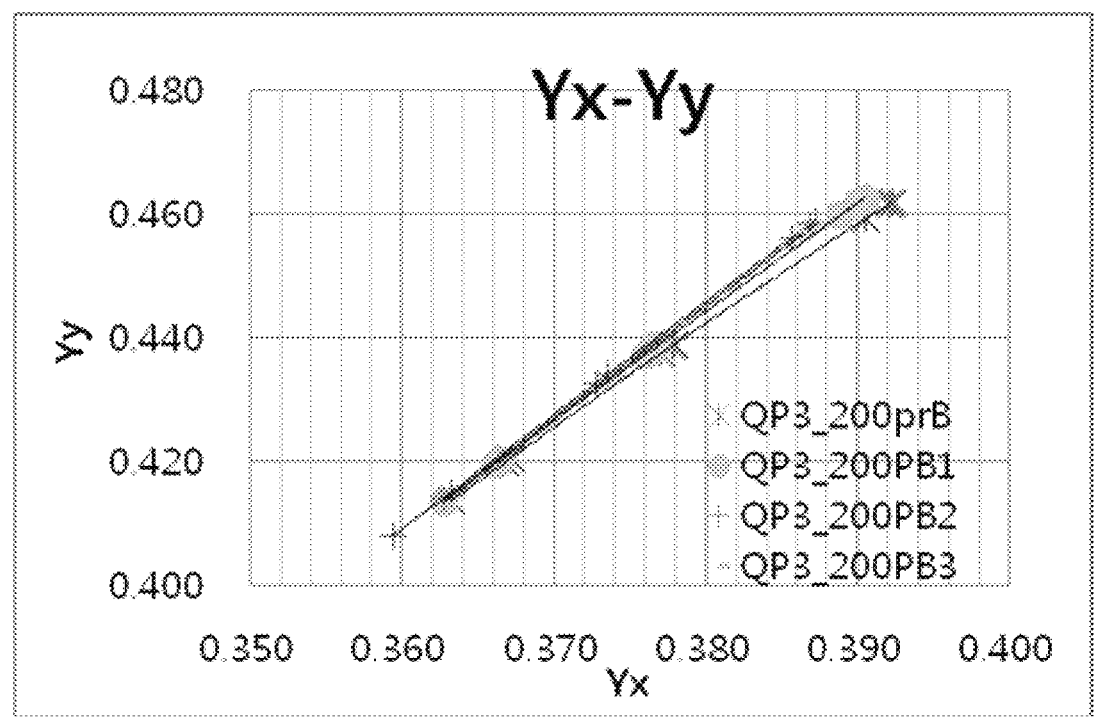
Figure 6D:
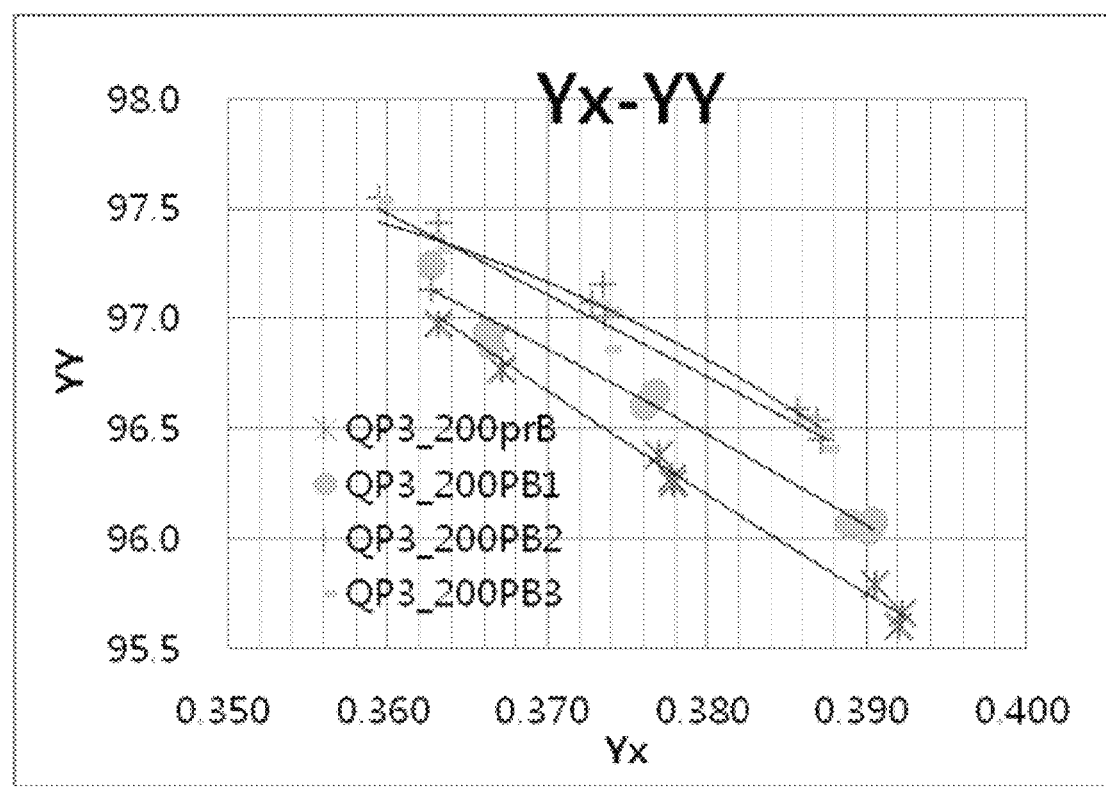
Figure 6E:
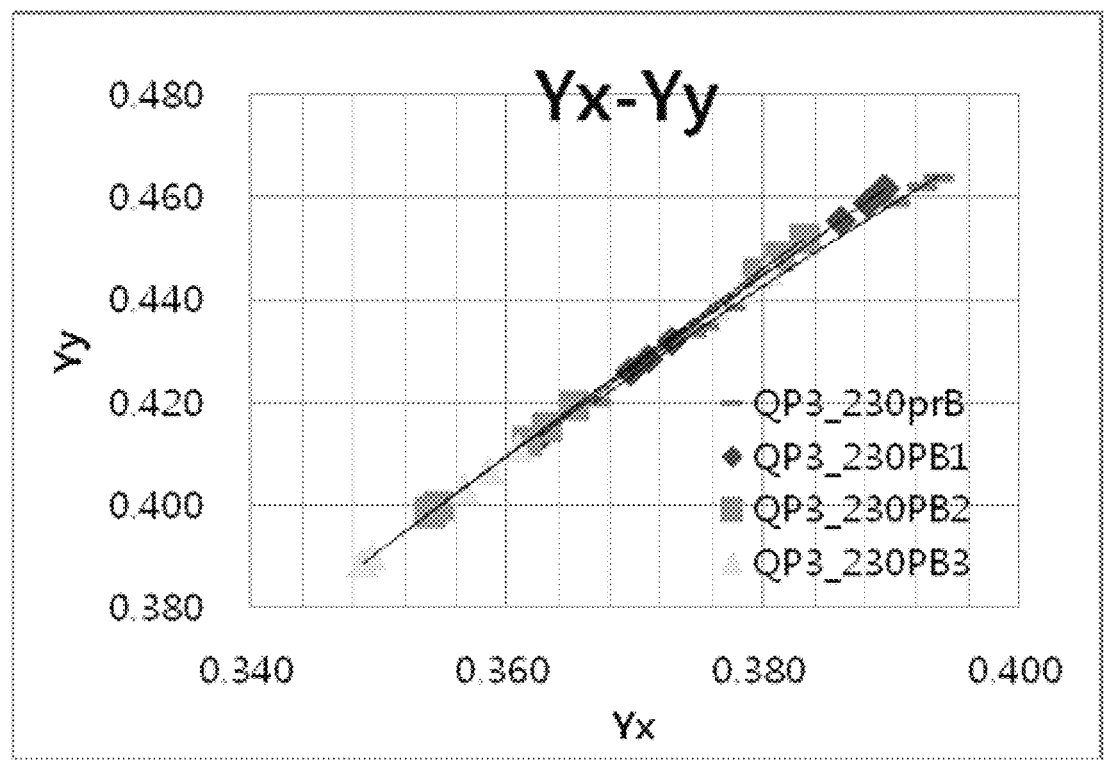
Figure 6F:
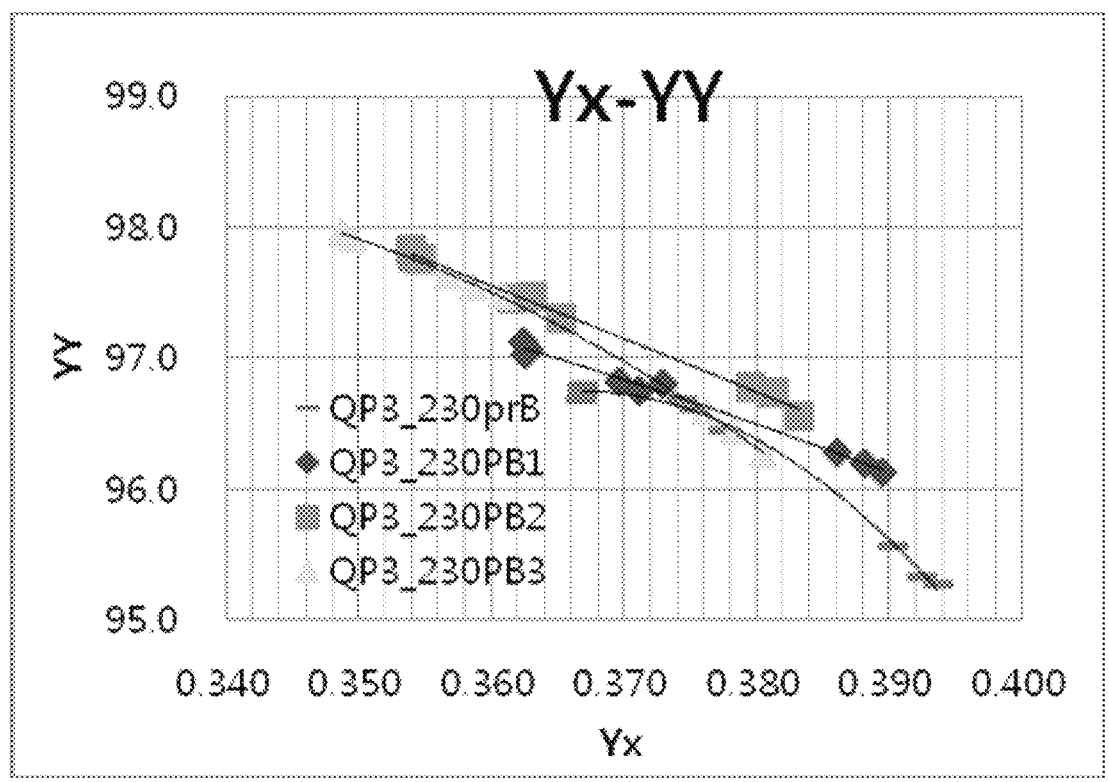

Spectrum changes by temperature of QP3 yellow dye were shown in FIGS. 5A-5C and Table 2.

TABLE 2

|  | spectroscopic change by # of PB (Δ Eab) |
|---|---|
| 180° C. | 0.36 → 1.84 → 1.98 |
| 200° C. | 0.56 → 2.74 → 2.77 |
| 230° C. | 2.94 → 9.3 → 13.4 |

It was found that solubility to PGMEA was 5-10%, the spectroscopic changes were good in treating at 180/200° C. and were stabilized according to increase of number. However, as shown in the red circle, spectroscopic changes at 230° C. were some large and were supposed to be caused by sublimation. In addition, it was shown that luminance was identical in comparison with Y138.

FIGS. 6A-6F show changes of color coordinate of QP3 depending on repetition of thermal process and changes of luminance value in state that the y coordinate is fixed. At first, it was found that overall tendency was insignificant at 180° C. On the contrary, it was identified that because at 200° C., there was a trend to be saturated according to repetition and positive effects that luminance increased with consistent wash-out of the color were shown, it was appropriate temperature to application. However, at 230° C., because the coordinate itself moved largely it seemed to be a intolerable temperature for the dye. In this analysis, QP3 had relatively lower change or coordinate and luminance raised according to repetition number of heat treatment, so these thermal resistance properties are considered to be ideal to be applied as a color filter.

Figure 7A:
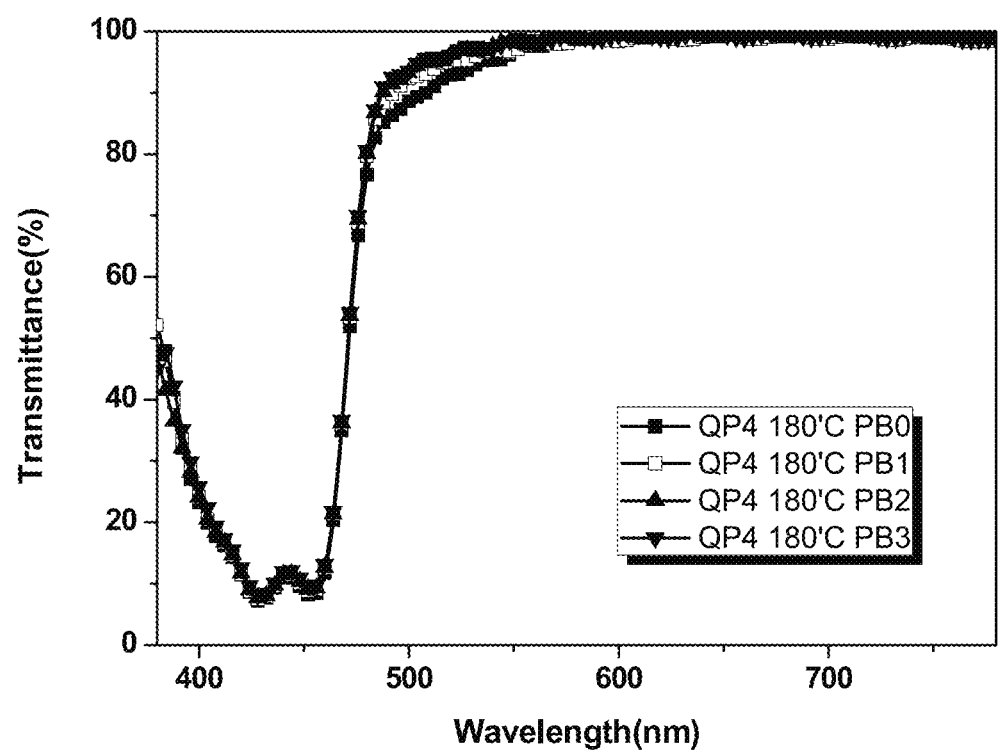
FIGS. 7A-7C are transmission spectrum graphs by number of PB of QP4.
Figure 7B:
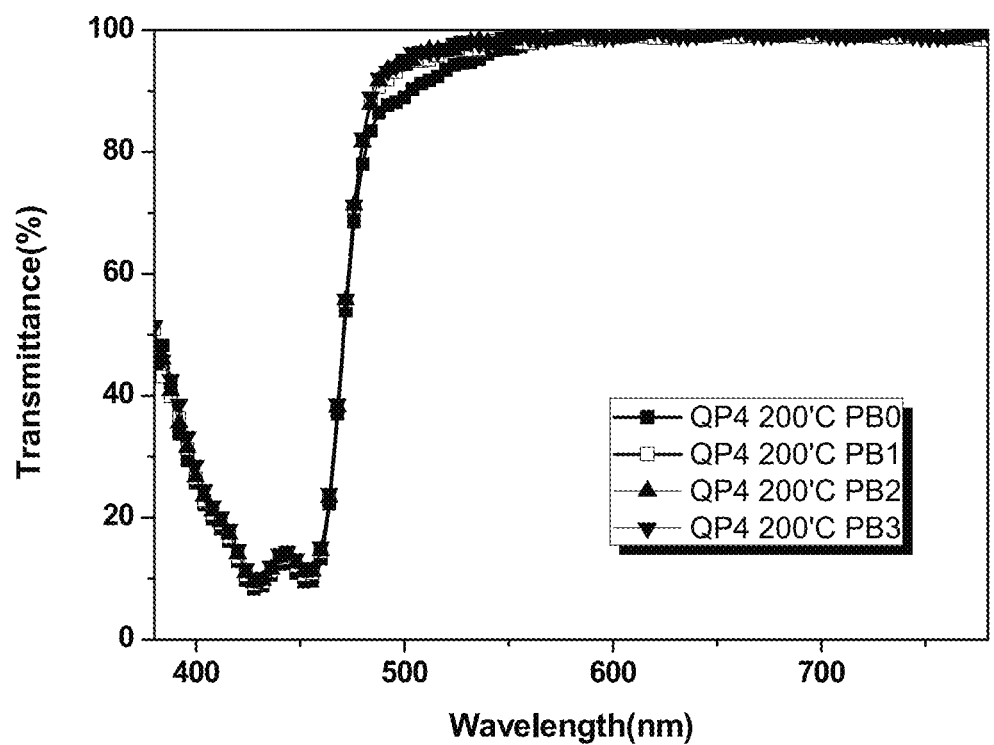
Figure 7C:
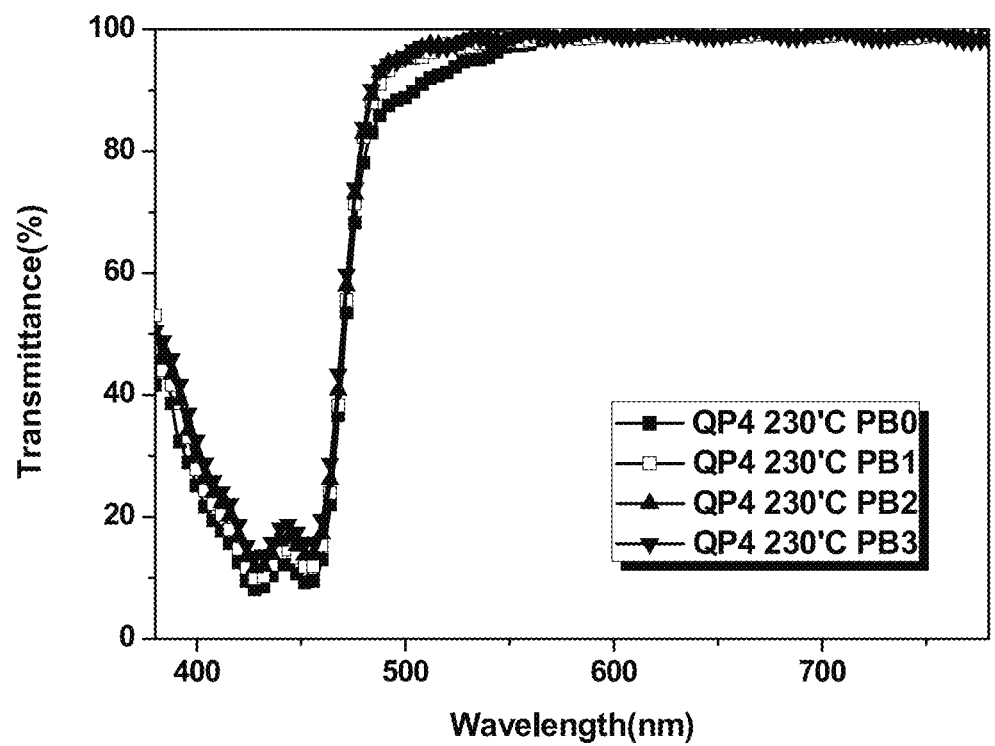
Figure 8A:
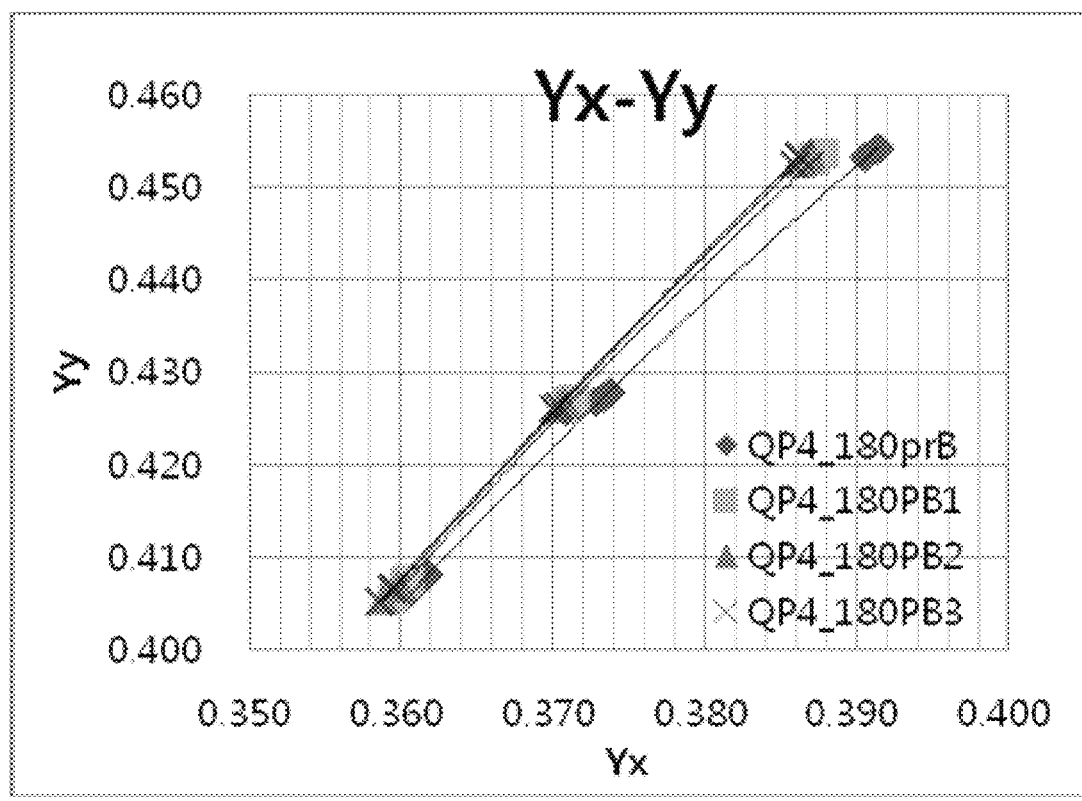
FIGS. 8A-8F are graphs showing color coordinate value change by temperatures of QP4.
Figure 8B:
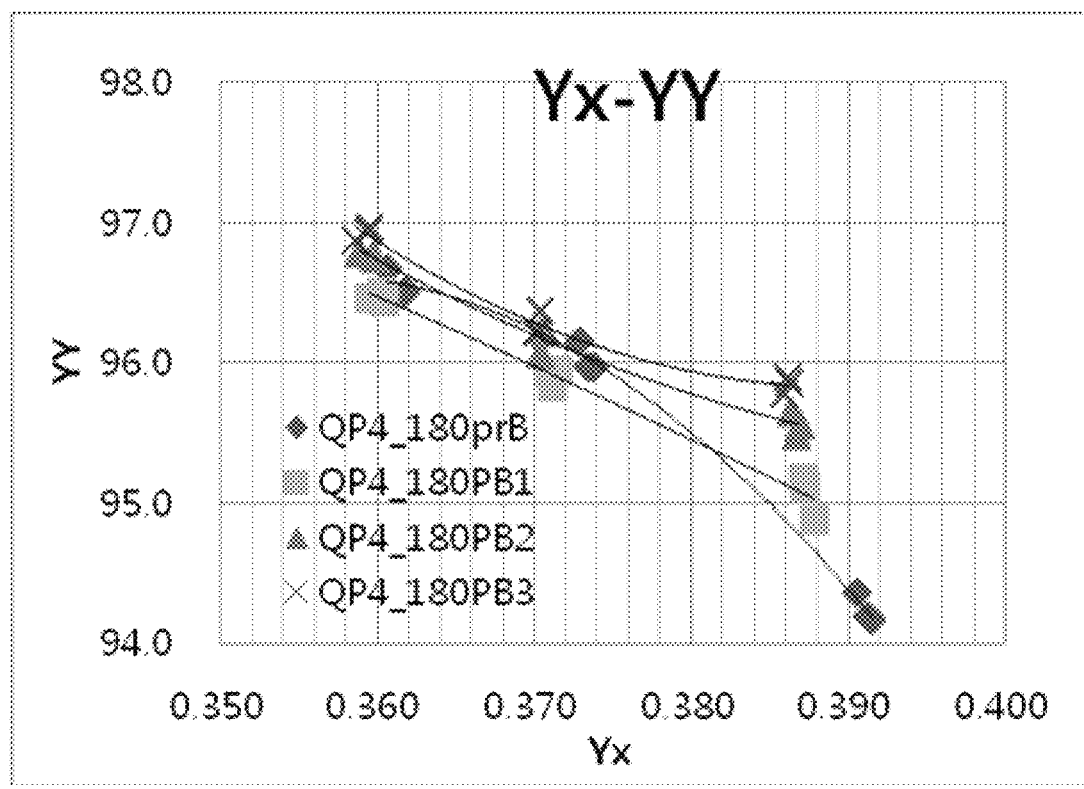
Figure 8C:
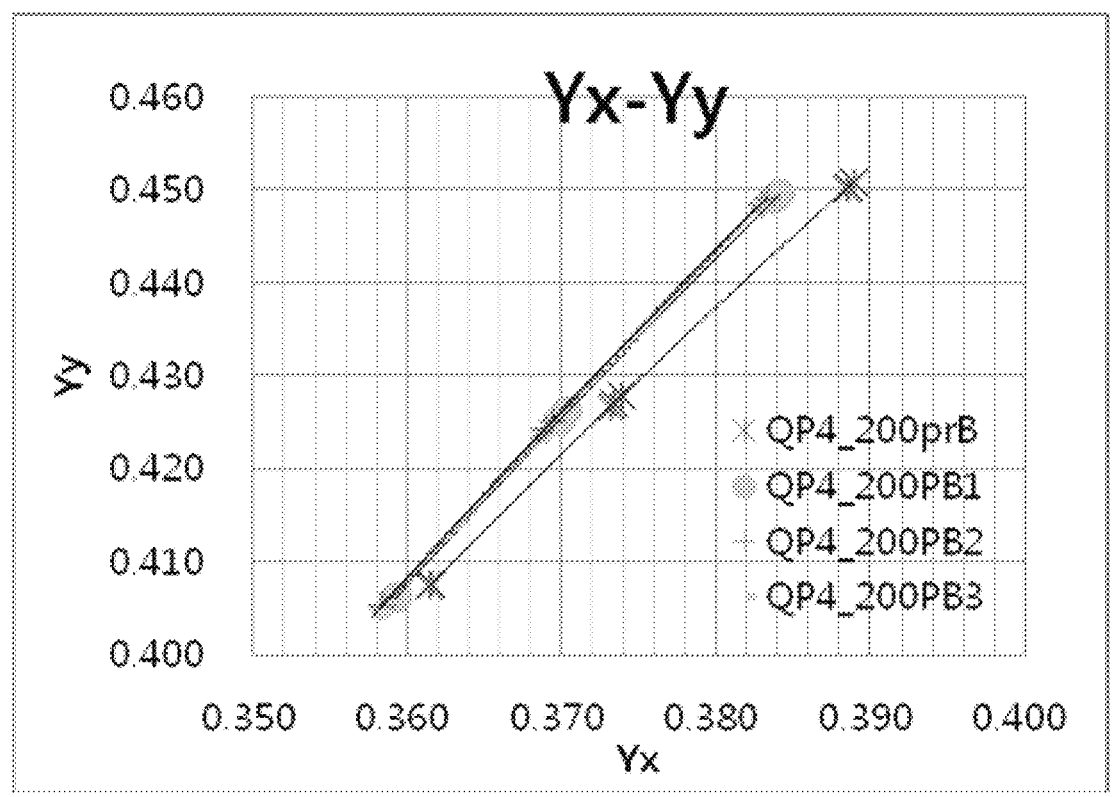
Figure 8D:
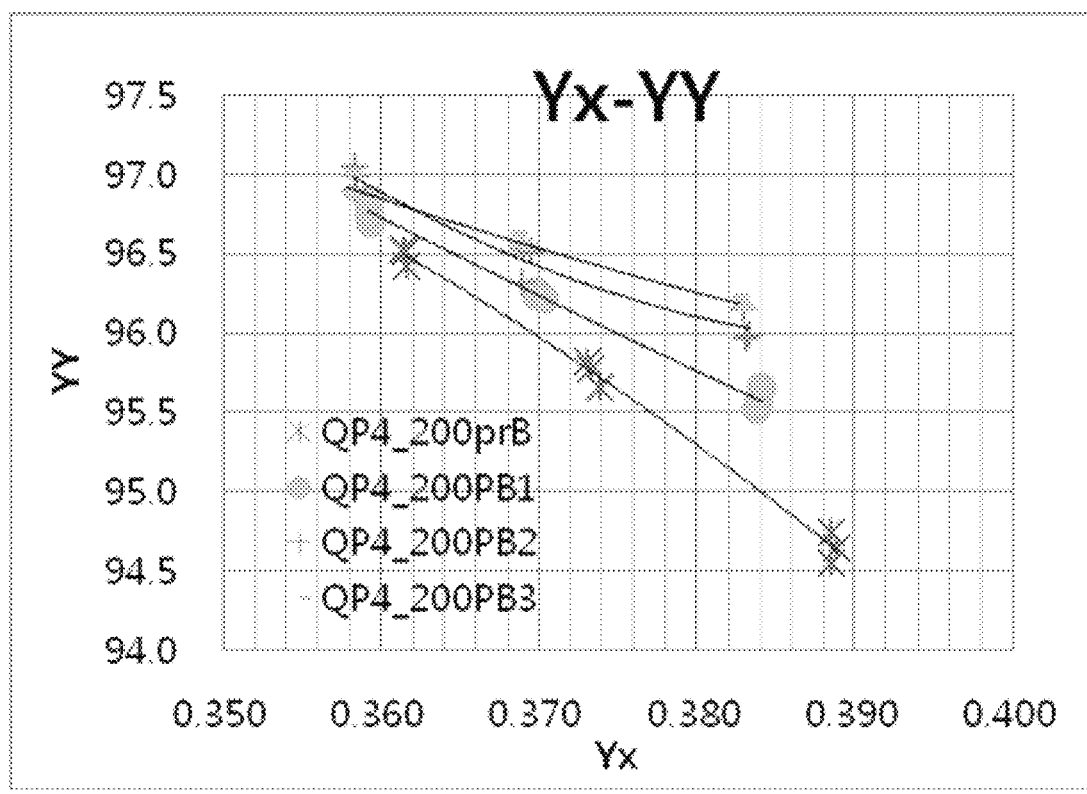
Figure 8E:
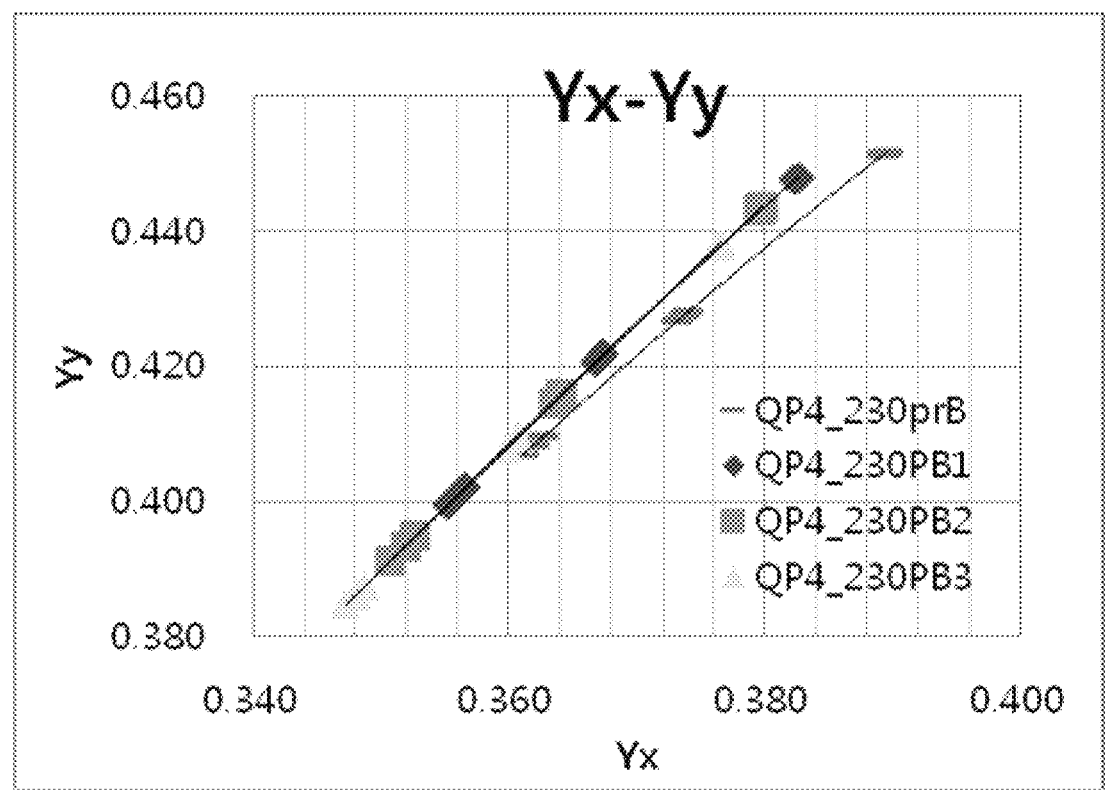
Figure 8F:
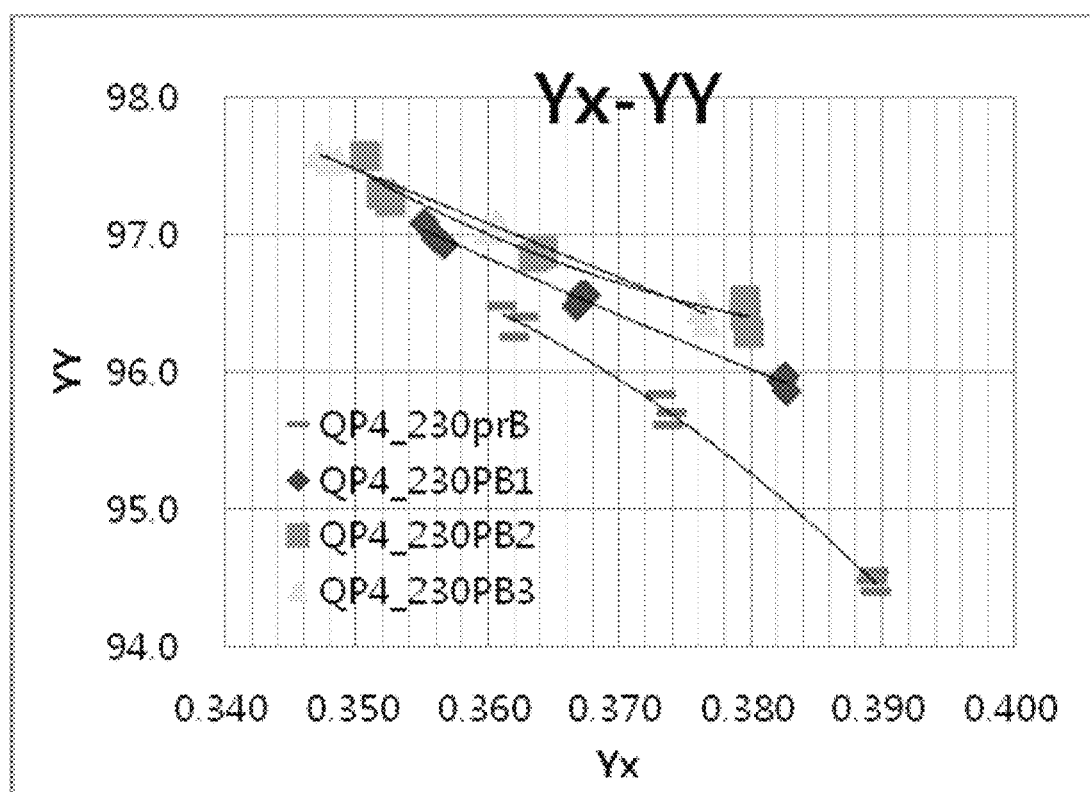

Spectrum changes by temperature of QP4 yellow dye were similar to QP3 and were shown in FIGS. 7A-7C and Table 3.

TABLE 3

|  | spectroscopic change by # of PB (Δ Eab) |
| --- | --- |
| 180° C. | 1.11 → 1.42 → 1.59 |
| 200° C. | 1.62 → 2.04 → 2.37 |
| 230° C. | 3.51 → 6.3 → 9.36 |

It was found that the solubility to PGMEA was 5-7%, the spectroscopic changes were good in treating at 180/200° C. and were stabilized according to increase of number. In treating at 230° C., the spectroscopic changes were severe and supposed to be caused by sublimation. It was found that luminance against Y138 was identical. As shown in spectroscopic changes by number of PB, it was identified that early thermal resistance of QP3 was not better than QP3, but it was saturated and got better according to increase of heat treatment number.

FIGS. 8A-8F show changes of color coordinate of QP3 depending on repetition of thermal process and changes of luminance value in state that the y coordinate is fixed. Luminance changes of QP4 were similar to QP3 as a whole but its tendency was relatively lower.

(3) Secondary Color Filter Application Property Assessment—Color Mixing Assessment of QP3 and QP4

Independent PR and color mixing assessment was performed for QP3 and QP4. Assessment condition was identical to the primary assessment.

Figure 9A:
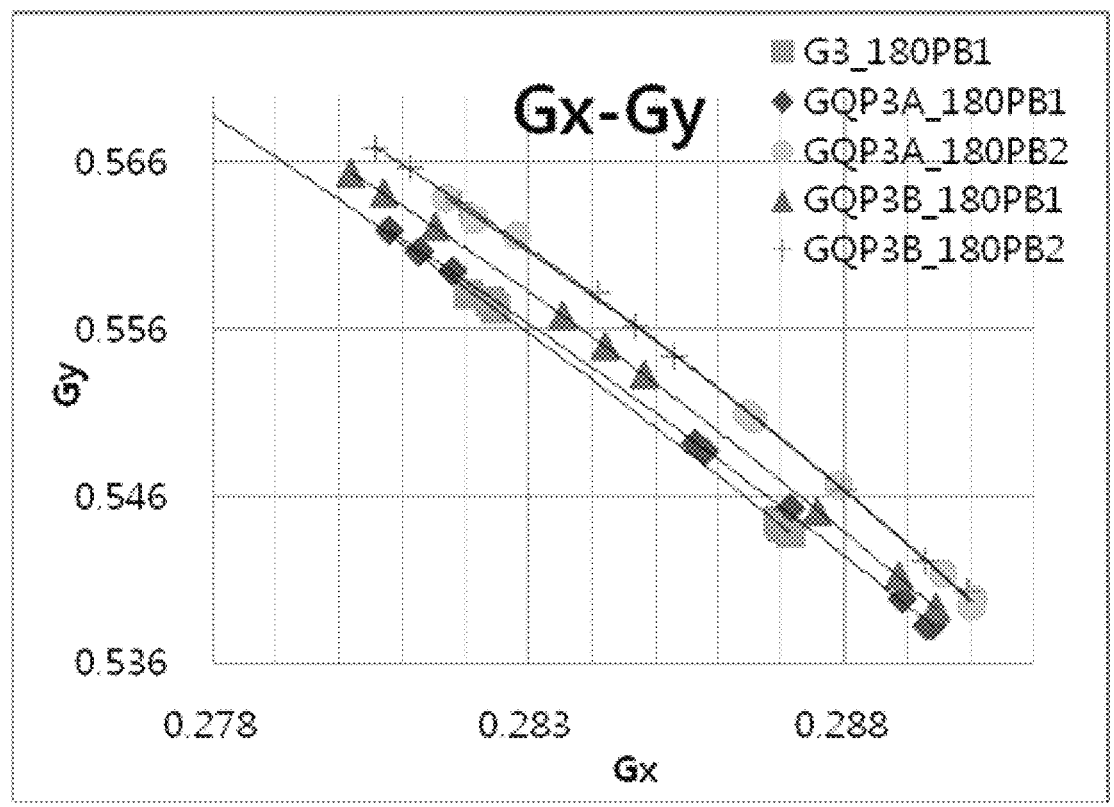
FIG. 9A and FIG. 9B are graphs showing color coordinate value change by temperatures in L binder of QP3.
Figure 9B:
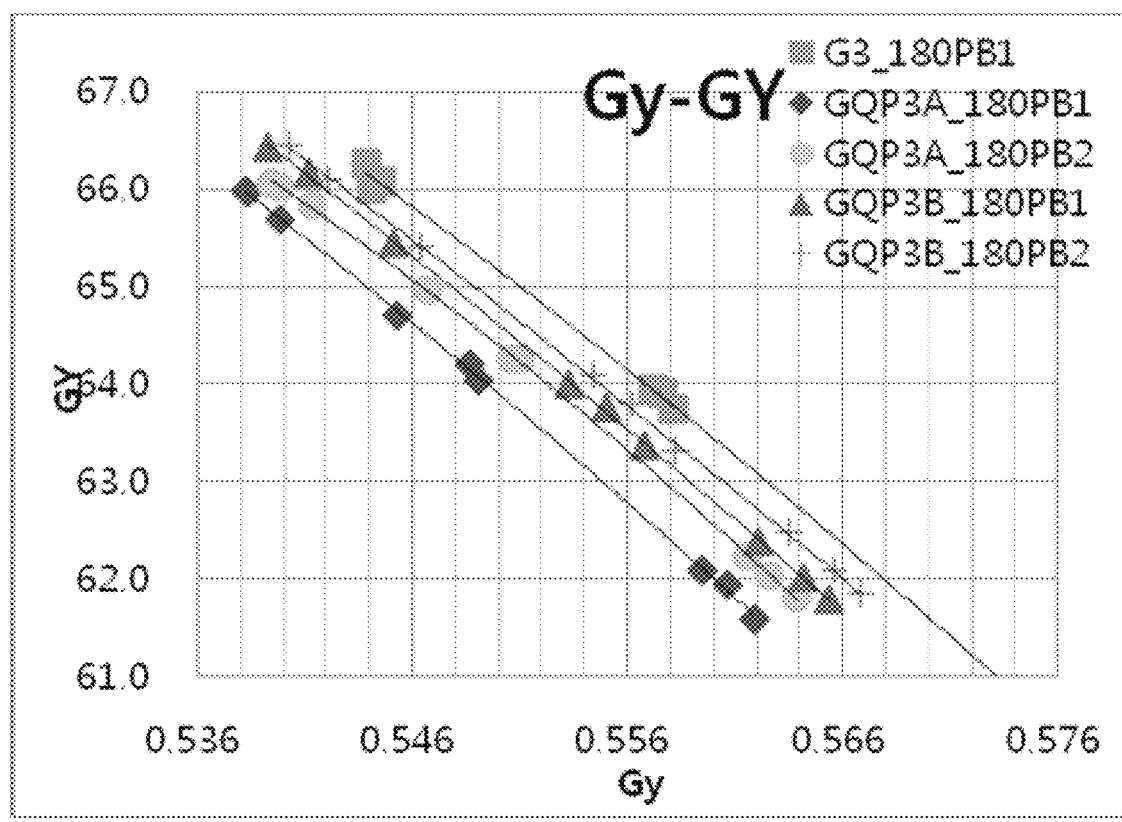

Color mixing assessment results of QP3 were shown in FIGS. 9A-9B and Table 4.

TABLE 4

| @Gx 0.283/ Gy 0.556 | Y138 replacement | G58/Y138/QP3 (%) | Binder | Gx | GY | modified GY | ΔGY vs. G3 |
| --- | --- | --- | --- | --- | --- | --- | --- |
| G3_180PB | 0% | 72/28/0 | L | 0.2829 | 64.15 | 64.17 | — |
| GQP3A_180PB1 | 100% | 76.5/0/23.5 | L | 0.2831 | 62.8 | 62.78 | ▼1.39 |
| GQP3A_180PB2 |  |  |  | 0.2847 | 63.35 | 63.01 | ▼1.16 |
| GQP3B_180PB1 | 50% | 74/13/13 | L | 0.28385 | 63.55 | 63.38 | ▼0.79 |
| GQP3B_180PB2 |  |  |  | 0.2847 | 63.8 | 63.46 | ▼0.71 |

Considering dispersibility of the dye, the assessment was performed dividing the substitution rate to 50% and 100% and binder L (normal linear type binder (including aromatic monomer)) was used. As the results, it was found that the luminance decreased in comparison with the pigment type and it was supposed to be caused by problems in compatibility with G58 MBS or compatibility with the binder. In addition, the luminance improvement effect at 180° C. after 2 times of PB shown in independent assessment was identified (A: +0.23/B: +0.08).

Figure 10A:
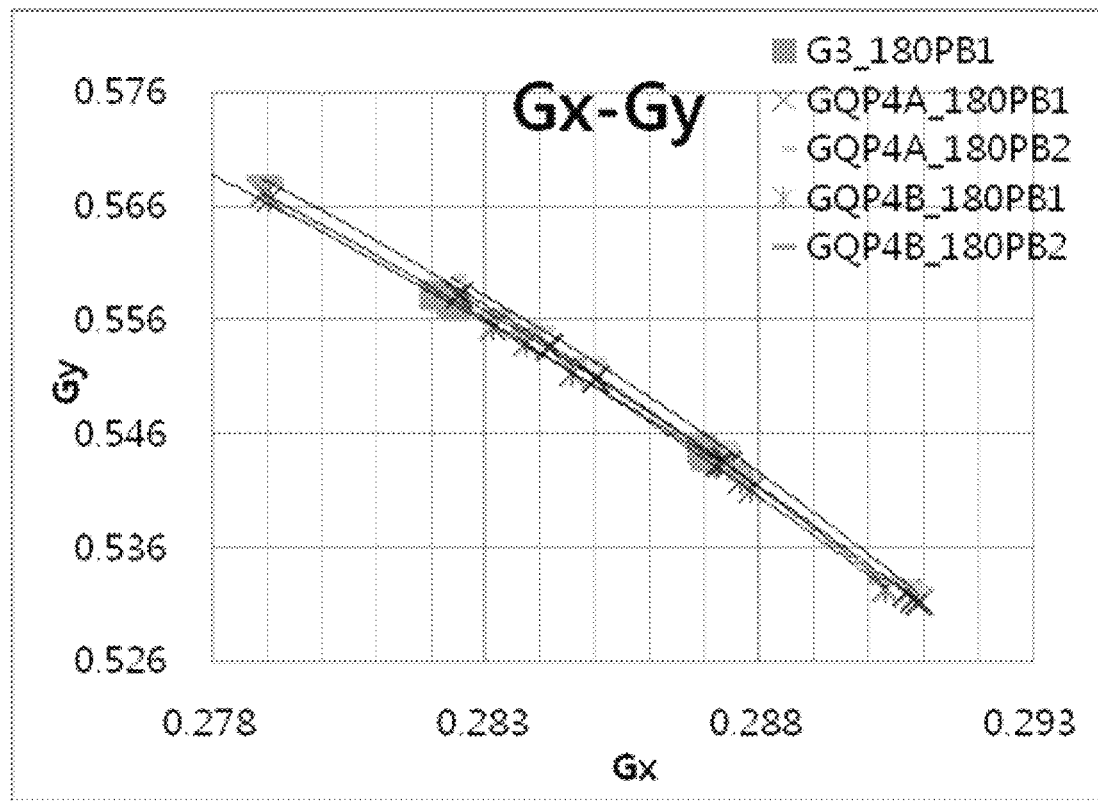
FIG. 10A and FIG. 10B are graphs showing color coordinate value change by temperatures of QP4.
Figure 10B:
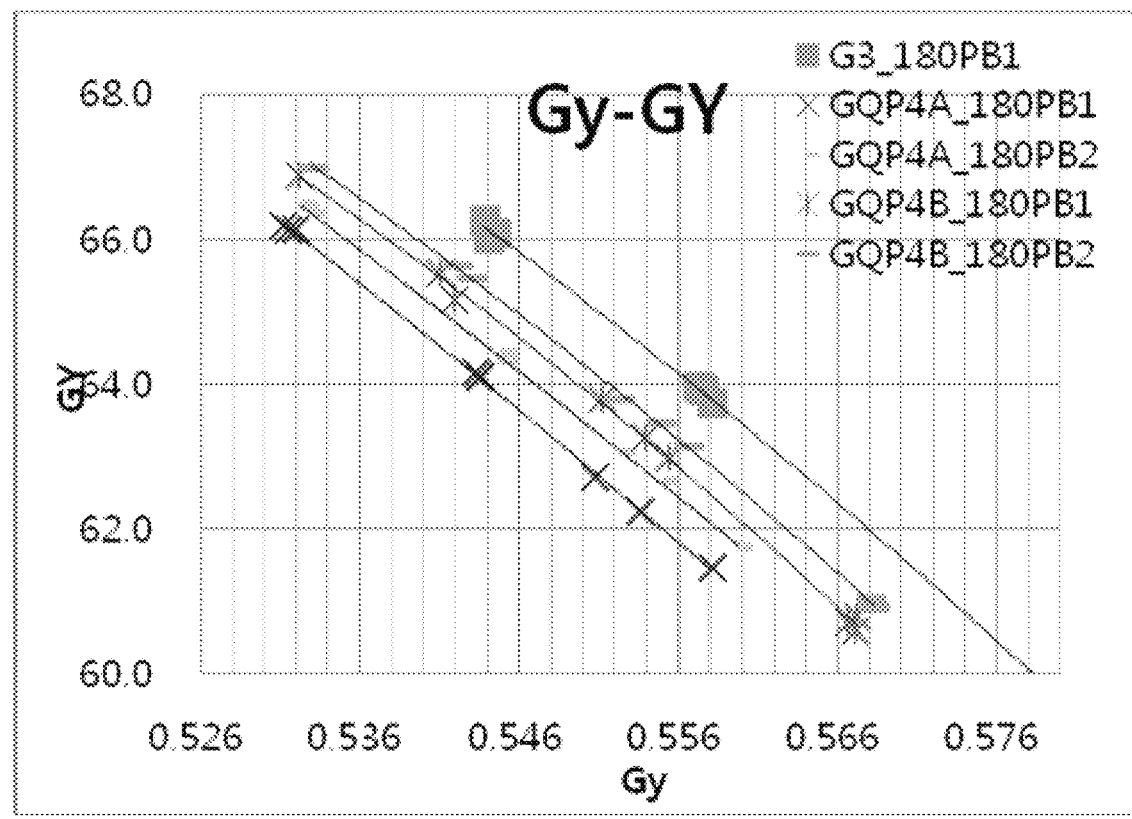

Color mixing assessment results in use of L-binder were shown in FIG. 10A-10B and below Table 5.

TABLE 5

| @Gx 0.283/ Gy 0.556 | Y138 replacement | G58/Y138/QP3 (%) | Binder | Gx | GY | modified GY | ΔGY vs. G3 |
| --- | --- | --- | --- | --- | --- | --- | --- |
| G3_180PB | 0% | 72/28/0 | L | 0.2829 | 64.15 | 64.17 | — |
| GQP4A_180PB1 | 100% | 75/0/25 | L | 0.2833 | 61.8 | 61.74 | ▼2.43 |
| GQP4A_180PB2 |  |  |  | 0.2837 | 62.45 | 62.31 | ▼1.86 |
| GQP4B_180PB1 | 50% | 74/13/13 | L | 0.283 | 62.85 | 62.85 | ▼1.32 |
| GQP4B_180PB2 |  |  |  | 0.2834 | 63.25 | 63.17 | ▼1.0 |

The luminance improvement effect at 180° C. after 2 times of PB was (A: +0.57/B: +0.32), which was higher than QP3.

Figure 11A:
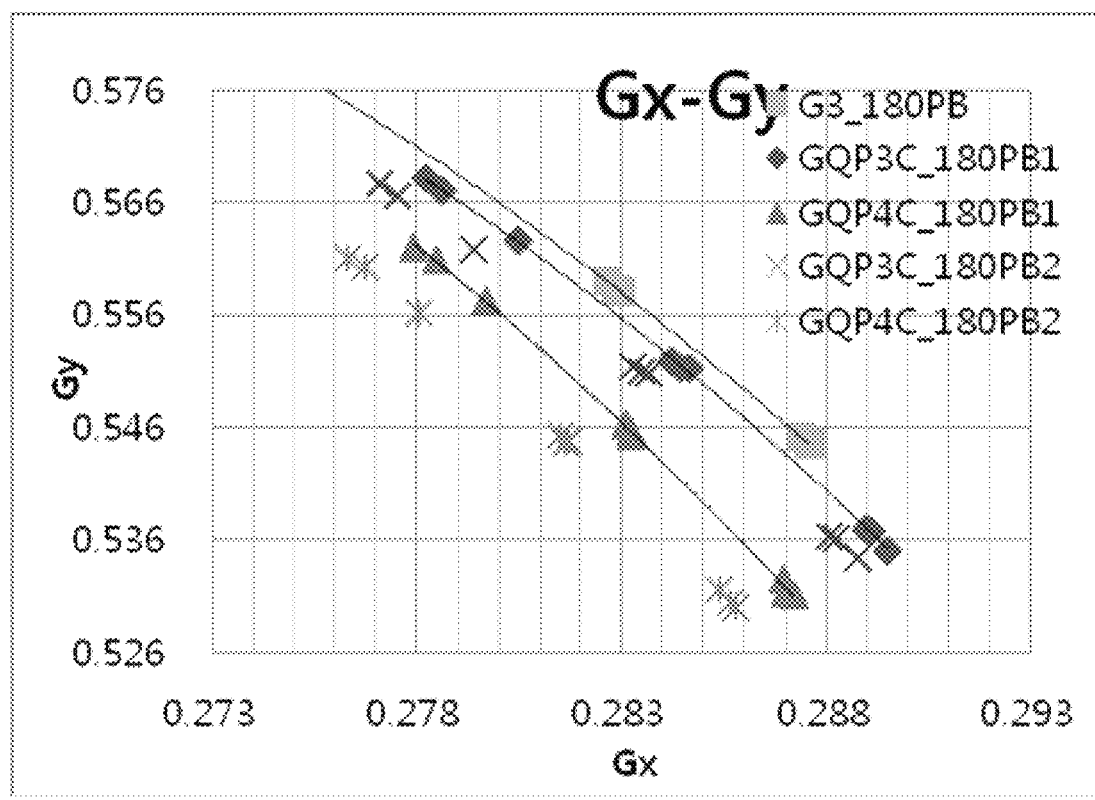
FIG. 11A and FIG. 11B are graphs showing color coordinate value change by temperatures in K binder of QP3 and QP4.
Figure 11B:
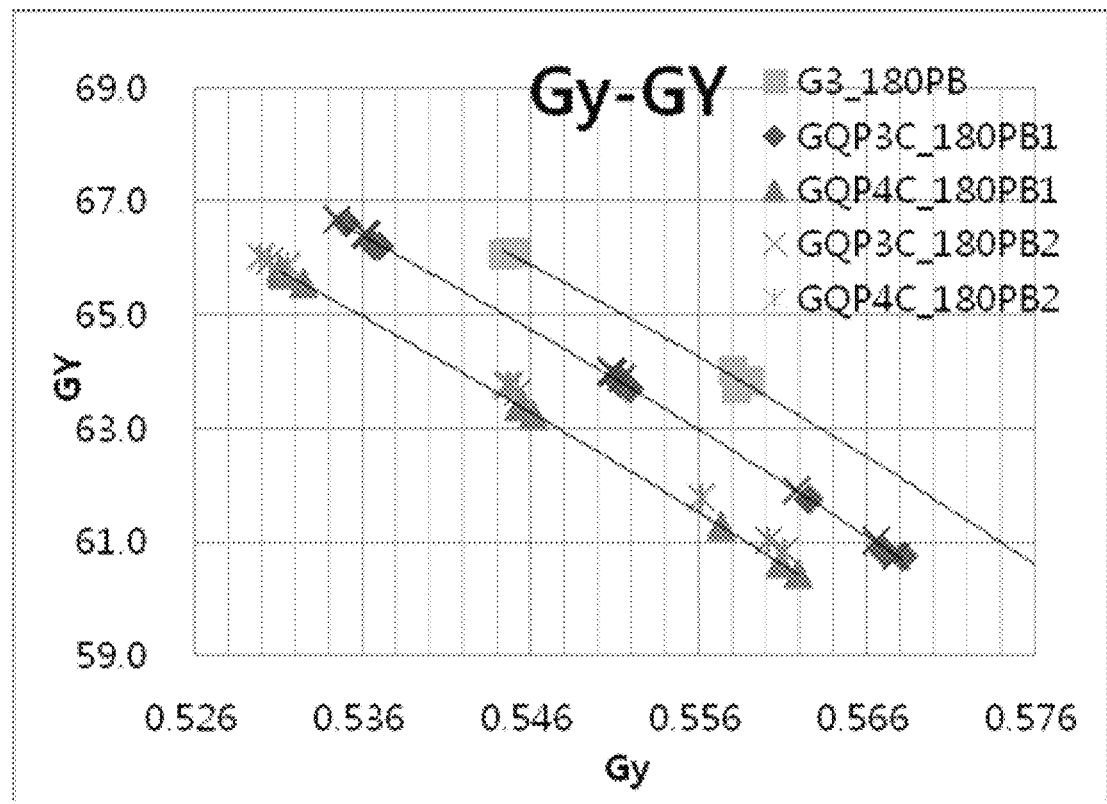

The results performed by changing the binder to Binder K (improved dye dispersion type) were shown in FIGS. 11A-11B and below Table 6.

TABLE 6

| @Gx 0.283/ Gy 0.556 | Y138 replacement | G58/Y138/QP3 (%) | Binder | Gx | GY | modified GY | ΔGY vs. G3 |
| --- | --- | --- | --- | --- | --- | --- | --- |
| G3_180PB | 0% | 72/28/0 | K | 0.2838 | 64.28 | 64.12 | — |
| GQP3C_180PB1 | 100% | 76.5/0/23.5 | K | 0.283 | 63 | 63 | ▼1.12 |
| GQP4C_180PB1 |  | 75/0/25 |  | 0.28 | 61.5 | 62.1 | ▼2.02 |
| G3_180PB | 0% | 72/28/0 | K | 0.283 | 63.9 | 63.9 | — |

TABLE 6-continued

| @Gx 0.283/ Gy 0.556 | Y138 replacement | G58/Y138/QP3 (%) | Binder | Gx | GY | modified GY | ΔGY vs. G3 |
|---|---|---|---|---|---|---|---|
| GQP3C_180PB2 | 100% | 76.5/0/23.5 | K | 0.2816 | 62.7 | 62.98 | ▼0.92 |
| GQP4C_180PB2 | | 75/0/25 | | 0.278 | 61.5 | 63.5 | ▼1.4 |

It was found that in comparison the pigment type the luminance was still lowered, but compared with use of L-binder, the luminance was improved somewhat. It seems that this is a result of compatibility increase with binder. On the basis of 1 time of PB, the luminance in comparison with use of L-binder increased as [+0.27(QP3)/+0.41(QP4)].

Figure 12A:
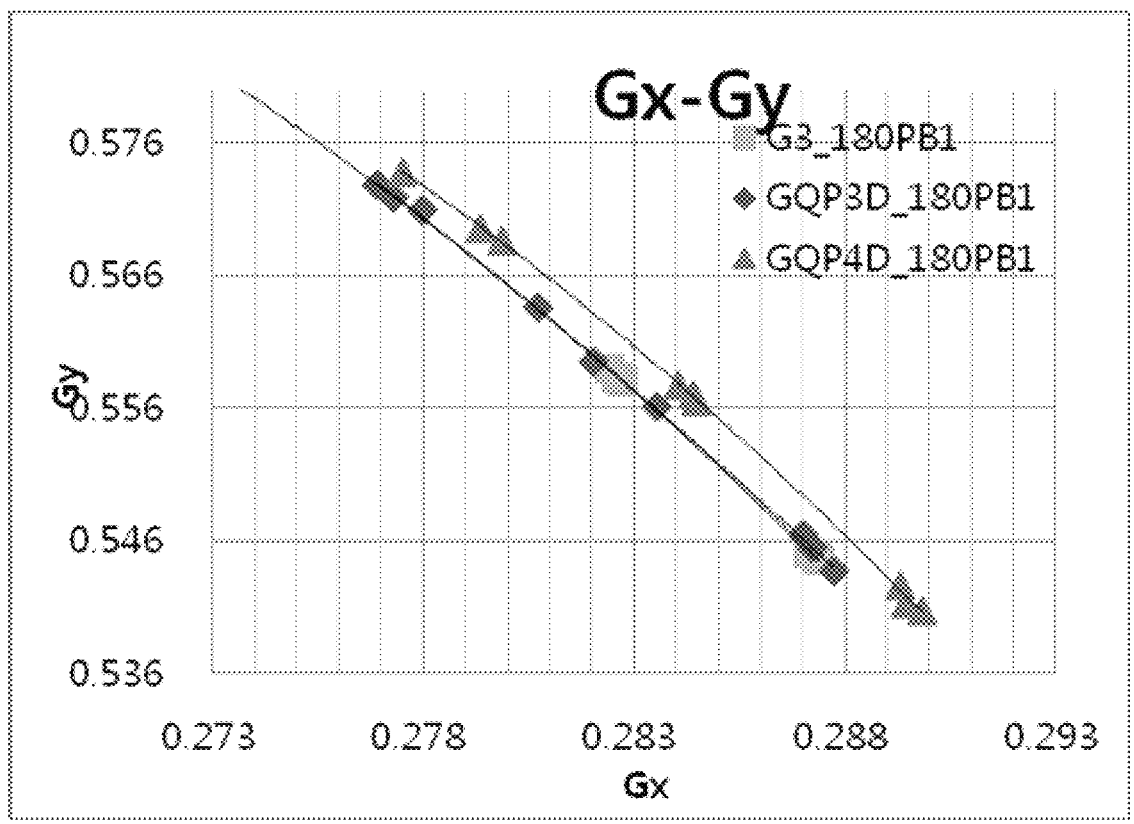
FIG. 12A and FIG. 12B are graphs showing color coordinate value change by temperatures in the mixing binder (K/S) of QP3 and QP4.
Figure 12B:
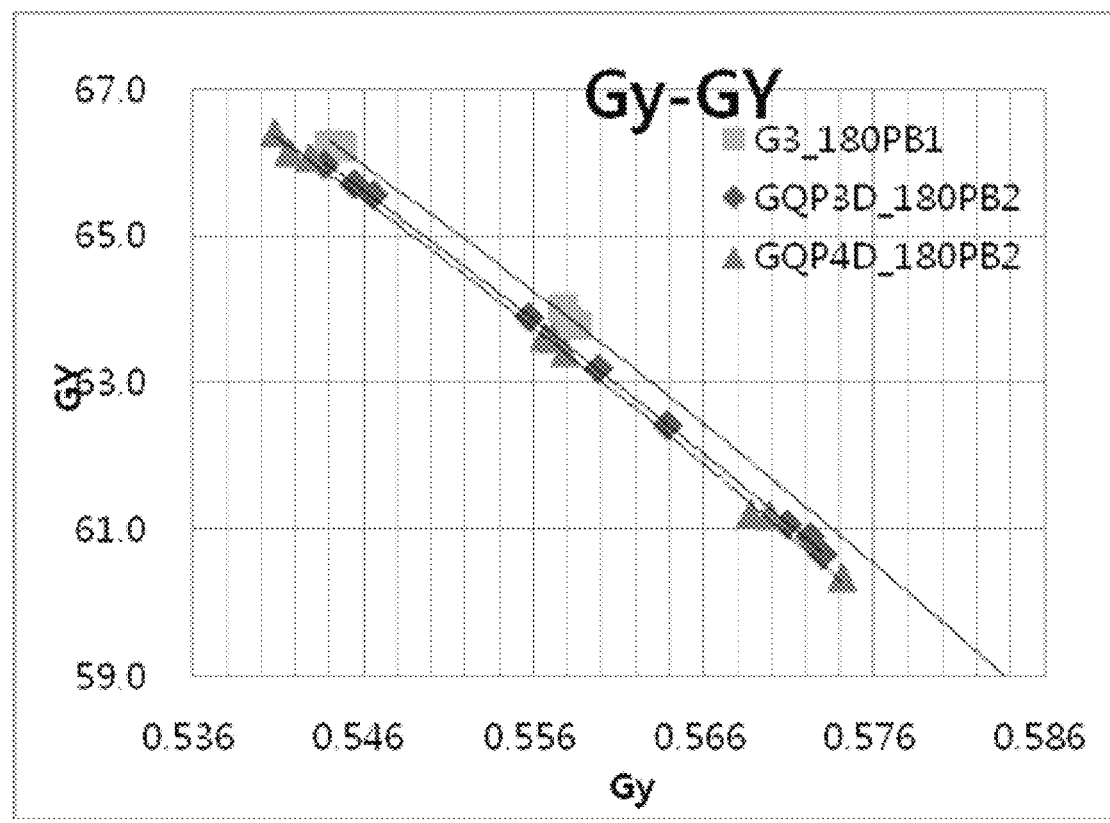

The color mixing assessment results in using S-binder designed as another dispersion improvement binder were shown in FIGS. 12A-12B and below Table 7.

TABLE 7

| @Gx 0.283/ Gy 0.556 | Y138 replacement | G58/Y138/QP3 (%) | Binder | Gx | GY | modified GY | ΔGY vs. G3 |
|---|---|---|---|---|---|---|---|
| G3_180PB | 0% | 72/28/0 | K/S | 0.2835 | 63.95 | 63.85 | — |
| GQP3D_180PB1 | 50% | 74/13/13 | K/S | 0.2835 | 63.55 | 63.45 | ▼0.4 |
| GQP4D_180PB1 | | 72/14/14 | | 0.2847 | 63.3 | 62.96 | ▼0.89 |
| G3_180PB | 0% | 72/28/0 | K/S | 0.2833 | 63.9 | 63.84 | — |
| GQP3D_180PB2 | 50% | 74/13/13 | K/S | 0.2833 | 63.5 | 63.44 | ▼0.4 |
| GQP4D_180PB2 | | 72/14/14 | | 0.2843 | 63.4 | 63.14 | ▼0.7 |

It was found that in comparison with the pigment type, the luminance decreased still and the decrease range of luminance by use of Y138 was reduced. On the basis of 1 time of PB, the luminance increased as [+0.39(QP3)/+0.62(QP4)] in comparison with GQP3B/GQP4B.

In order to identify decrease of transmittance according to dispersion insufficiency and dye crystallization, Contrast Ratio (CR) measurement results were shown in Table 8.

TABLE 8

| @Gx 0.283/ Gy 0.556 | Y138 replacement | G58/Y138/QP3 (%) | Binder | vs. after PB | vs. pigment (before PB) | vs. pigment (after PB) |
|---|---|---|---|---|---|---|
| G3 | 0% | 72/28/0 | K/S | 91.3% | — | — |
| GQP3C | 100% | 76.5/0/23.5 | K/S | 82.8% | 108.1% | 98.1% |
| GQP3D | 50% | 74/13/13 | | 95.3% | 95.6% | 99.8% |
| GQP4C | 100% | 76.5/0/23.5 | K/S | 69.1% | 115.6% | 87.5% |
| GQP4D | 50% | 72/14/14 | | 87.8% | 102.6% | 98.6% |

It was found that in comparison with the pigment type, CR value difference before and after PB was relatively large, which was remarkable in use of QP4. When comparing the pigment type and CR value, it was identified that the dye was controlled below the pigment particle size before heat treatment, but the size control was failed after heat treatment. In other words, it supported that an effort to maintain particle size with application of dispersing agent was needed. For more accurate analysis, although comparison and identification after CR measurement with dye independent PR are needed, it was identified visibly that when the dye content was higher, the film surface was more haze.

Figure 13A:
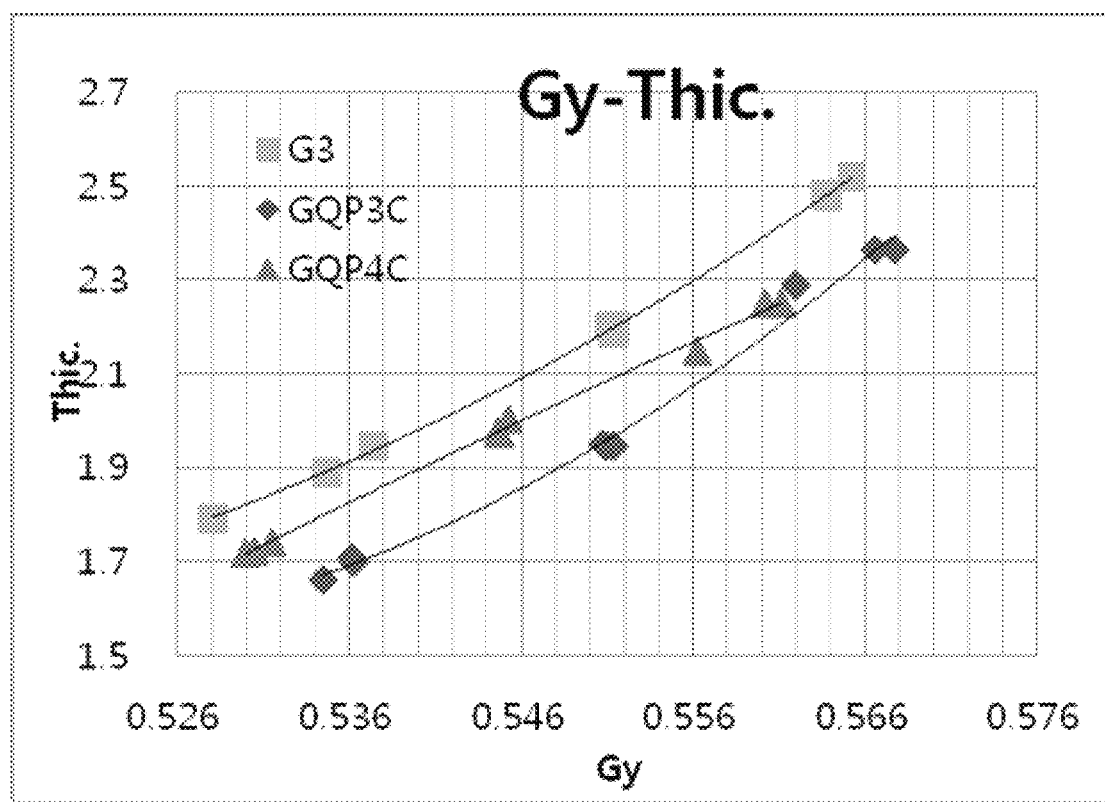
FIG. 13A and FIG. 13B are coloring assessment graphs of QP3 and QP4.
Figure 13B:
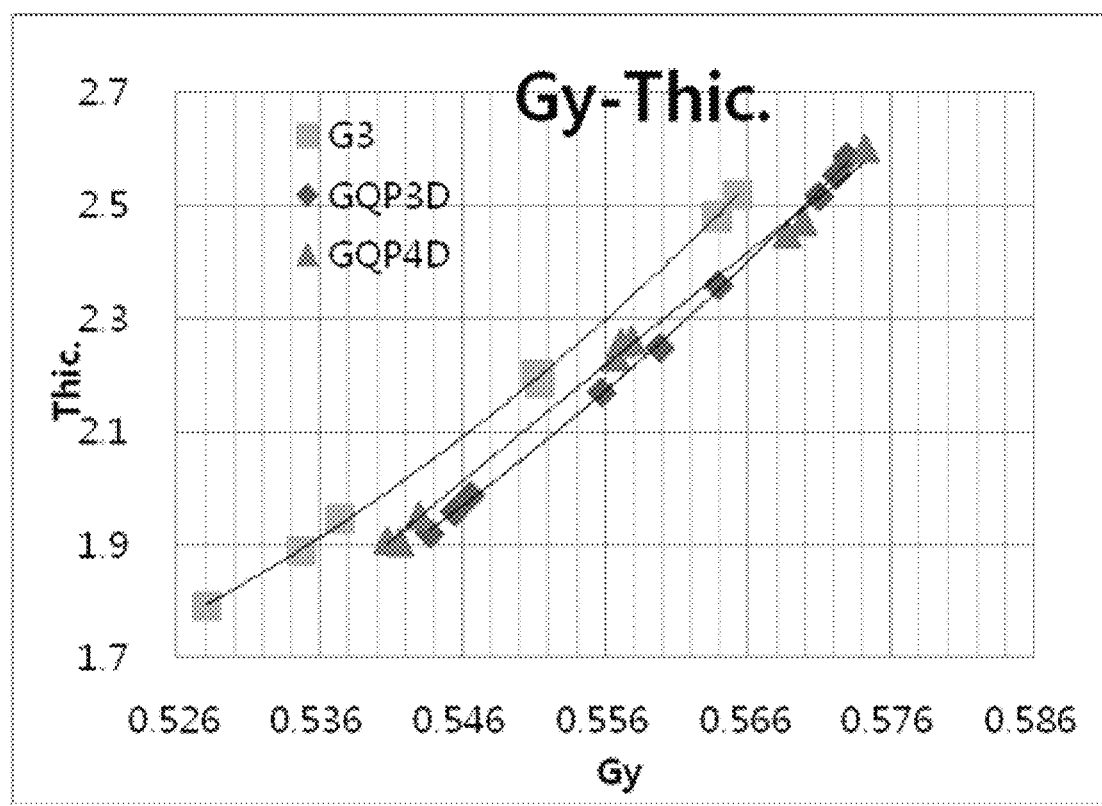

Coloring assessment results of QP3 and QP4 were shown in FIGS. 13A-13B and below Table 9.

TABLE 9

| @Gx 0.283/ Gy 0.556 | Y138 replacement | G58/Y138/QP3 (%) |
|---|---|---|
| G3_180PB | 0% | 72/28/0 |
| GQP3C_180PB | 100% | 76.5/0/23.5 |
| GQP3D_180PB | 50% | 74/13/13 |

TABLE 9-continued

| @Gx 0.283/ Gy 0.556 | Y138 replacement | G58/Y138/QP3 (%) |
|---|---|---|
| GQP4C_180PB | 100% | 75/0/25 |
| GQP4D_180PB | 50% | 72/14/14 |

When substituting dye instead of Y138, the coloring force was excellent in comparison with the pigment type and it seems to be caused by high molar extinction coefficient. Especially, it was identified that the color thickness decreased as much as 2 um in 100% substitution.

Figure 14A:
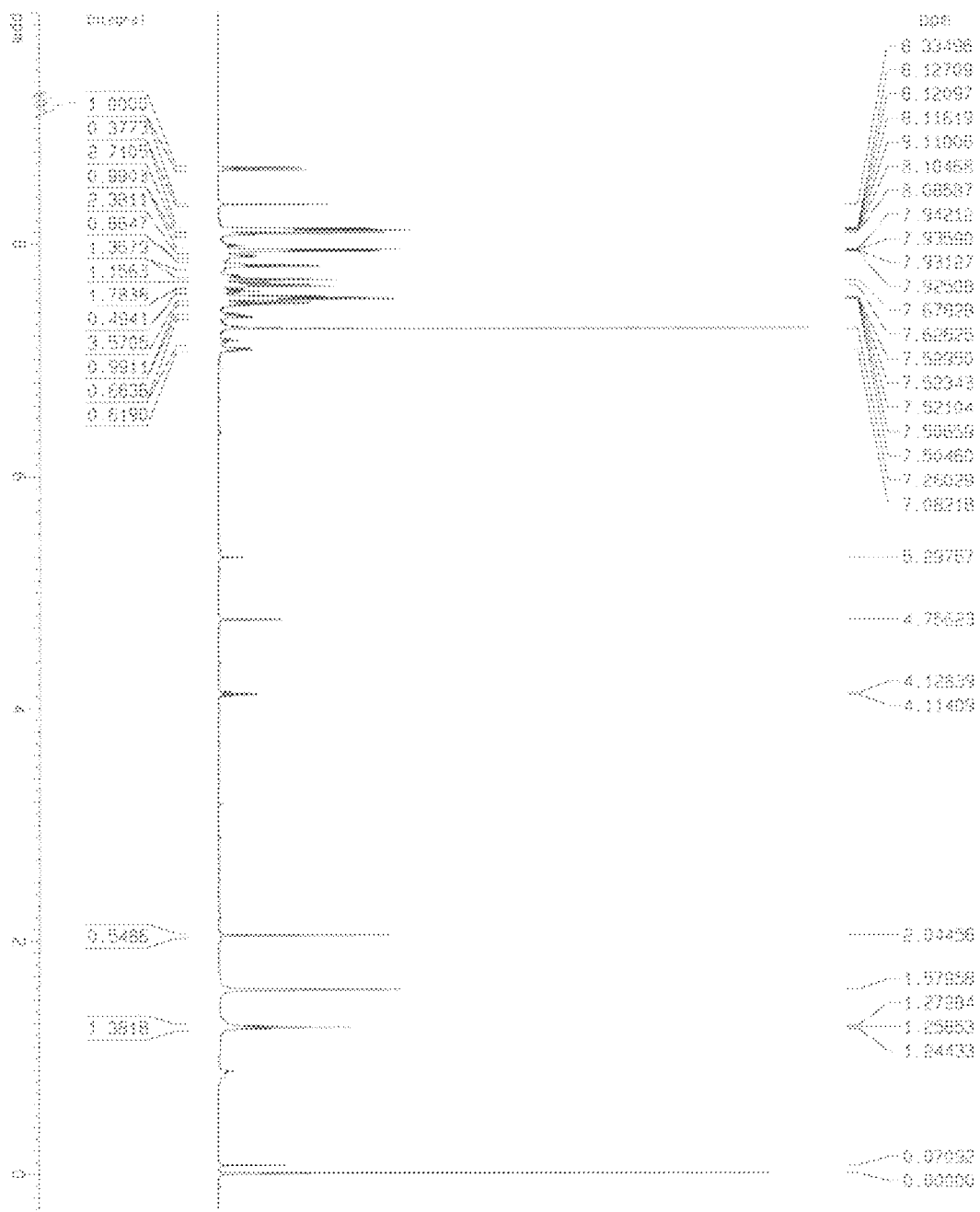
FIG. 14A is a NMR result confirming synthesis of QP1.
Figure 14B:
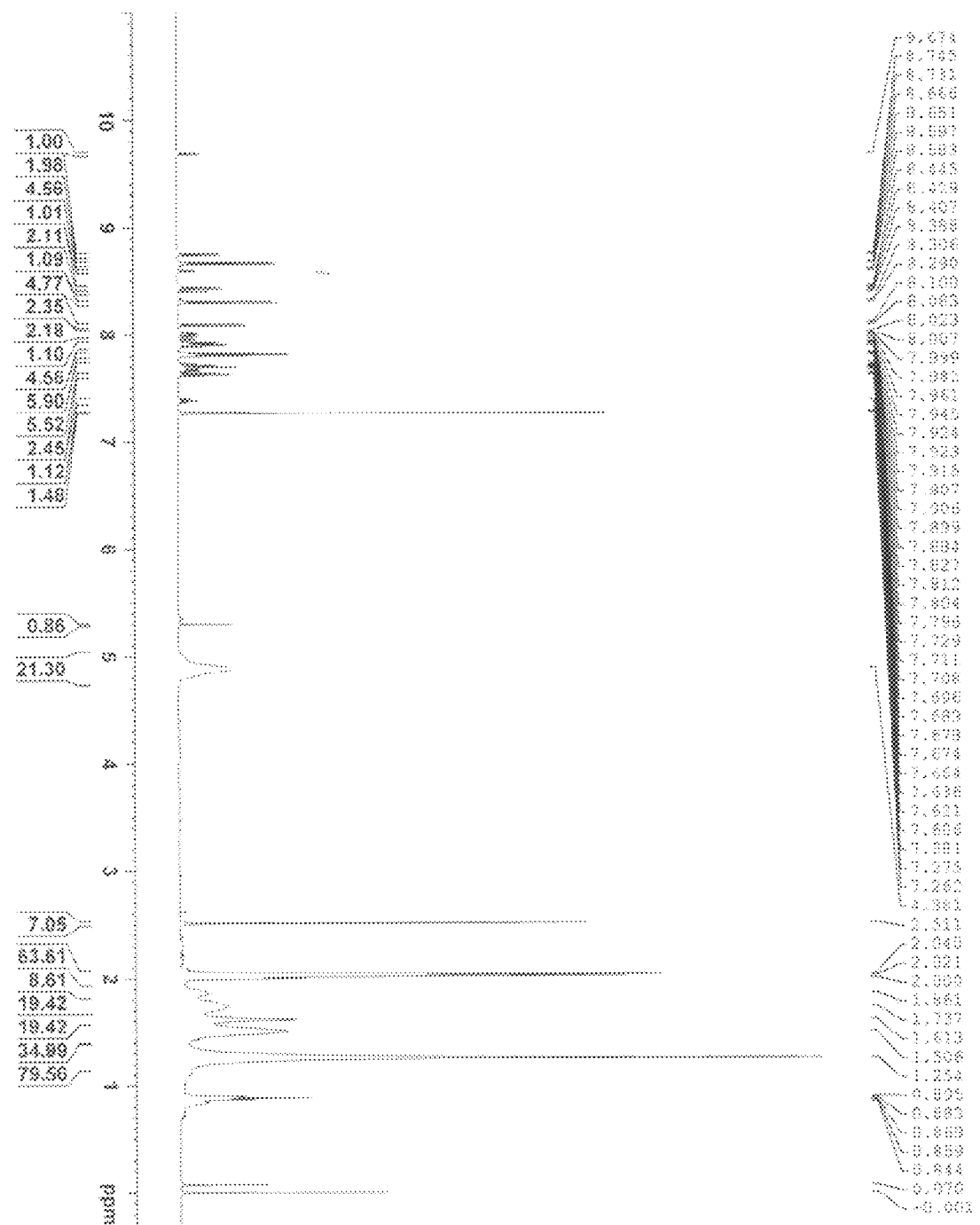
FIG. 14B is a NMR result confirming synthesis of QP2.
Figure 14C:
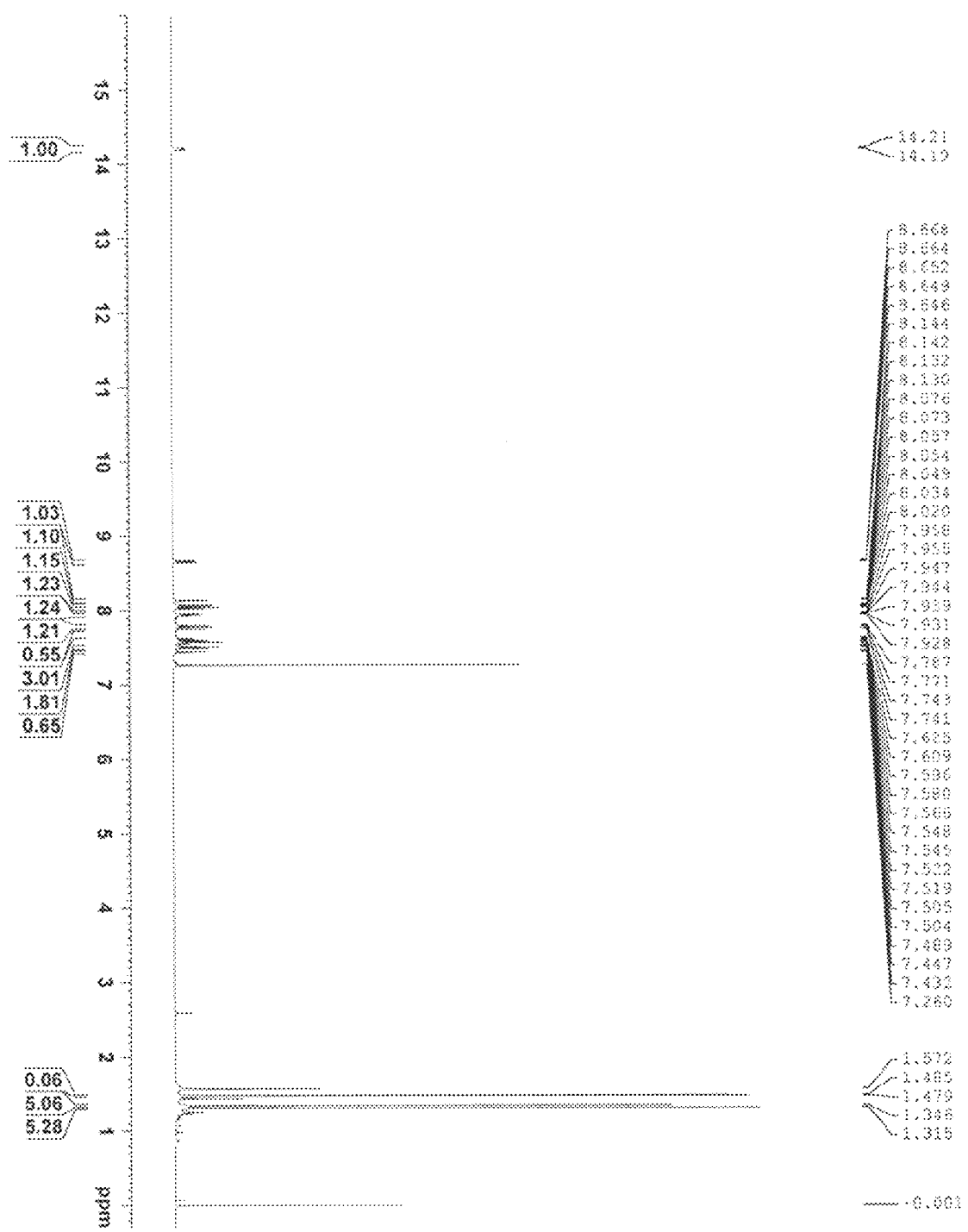
FIG. 14C is a NMR result confirming synthesis of QP3.
Figure 14D:
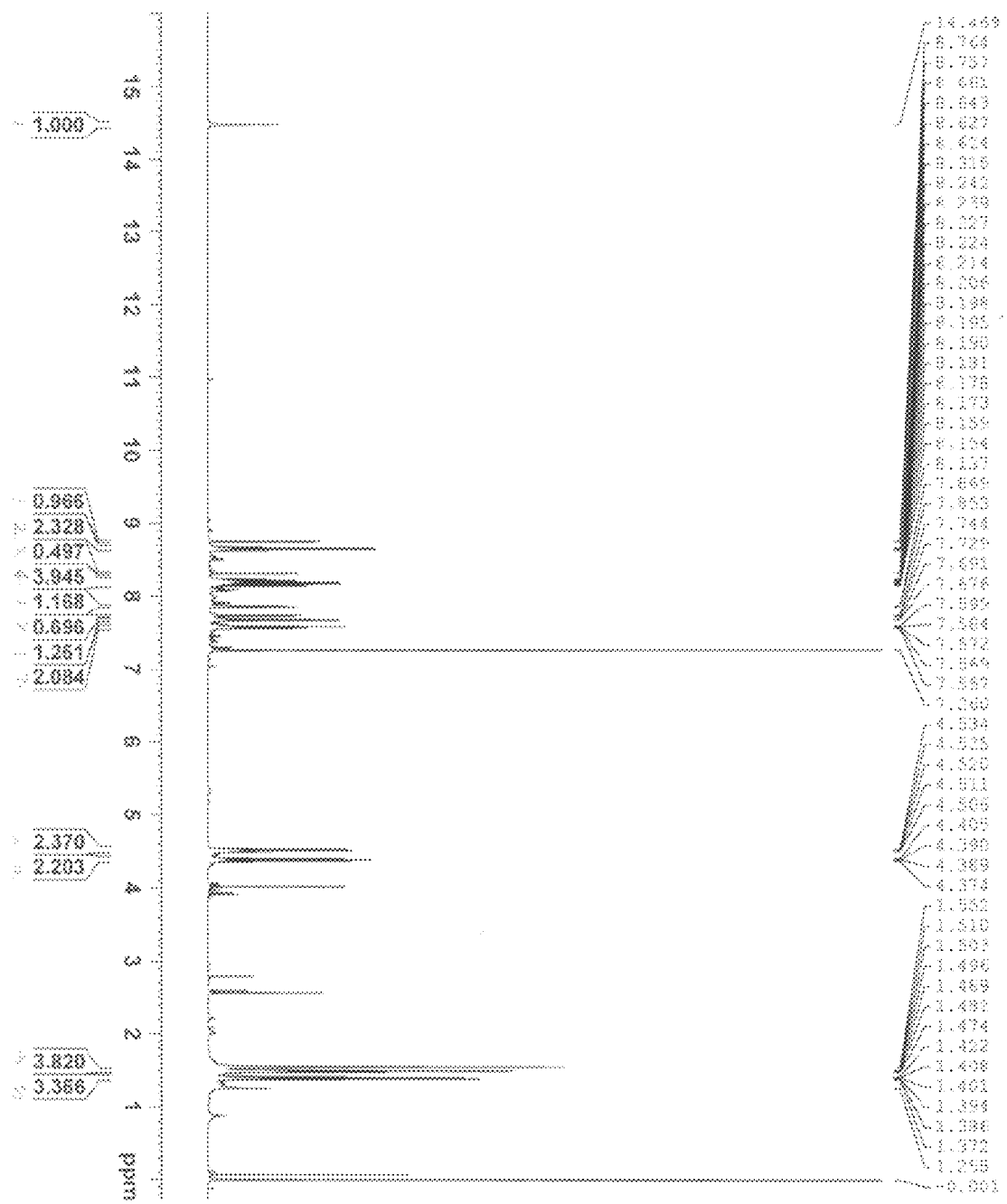
FIG. 14D is a NMR result confirming synthesis of QP4.
Figure 14E:
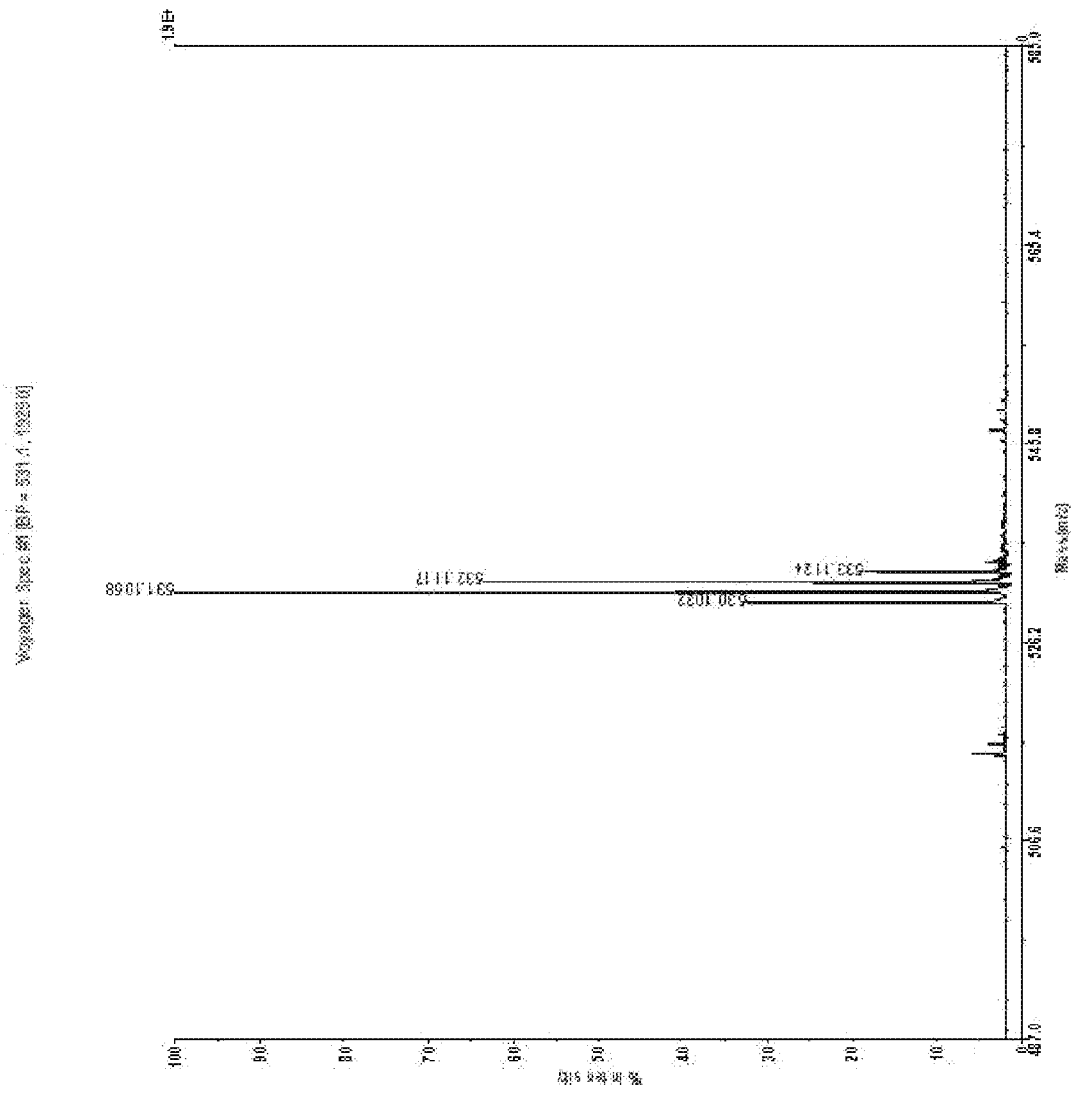
FIG. 14E is a MALDI-TOF result confirming synthesis of QP3.
Figure 14F:
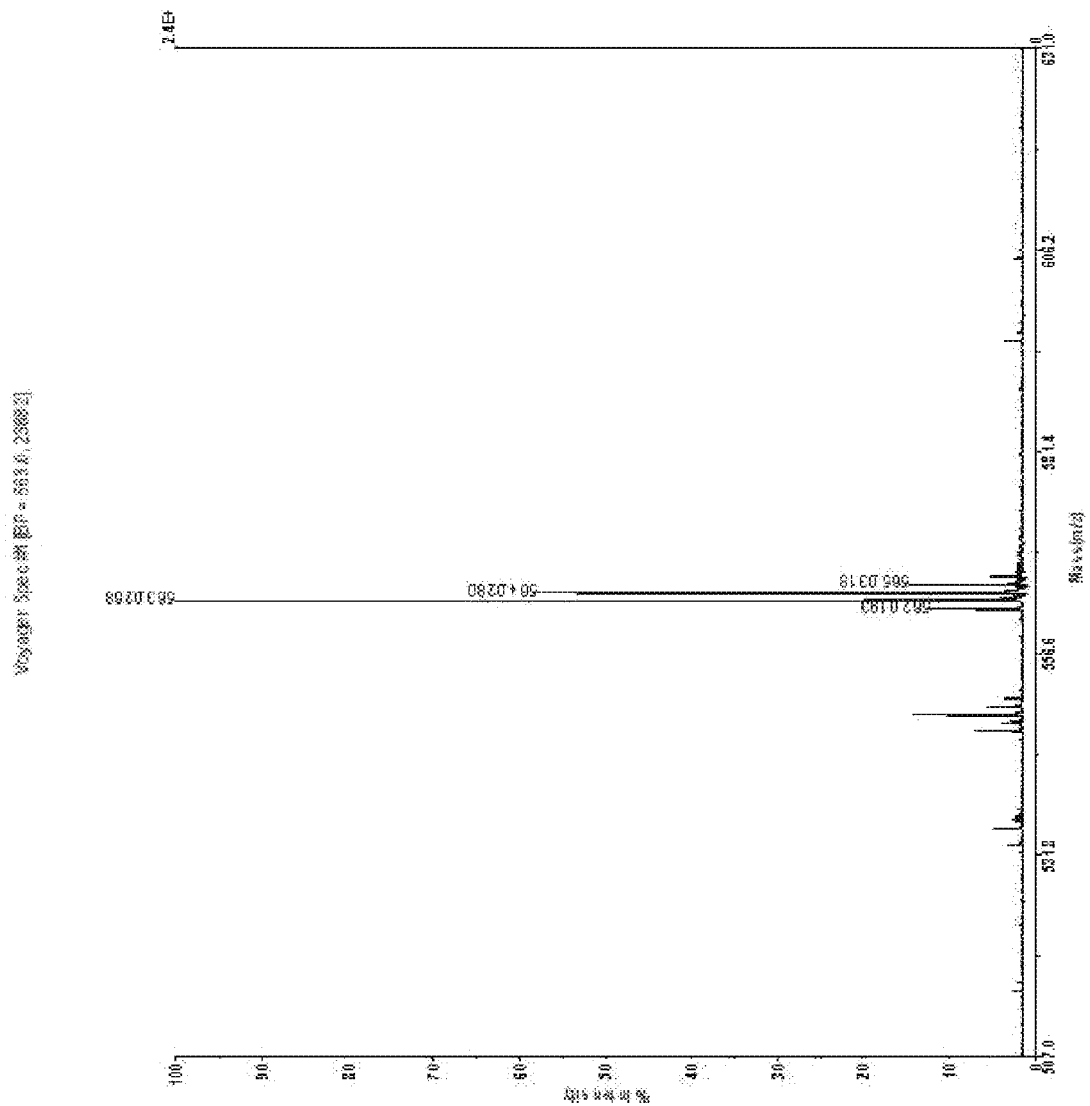
FIG. 14F is a MALDI-TOF result confirming synthesis of QP4.

Also, FIGS. 14A-14D show examples of NMR results confirming synthesis of QP1, QP2, QP3 and QP4, respectively, while FIGS. 14E and 14F show examples of MALDI-TOF results confirming synthesis of QP3 and QP4, respectively.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within

What is claimed is:

1. A dye comprising a compound of Formula 1:

[Structure of Formula (1) showing a quinoline-indanedione-phthalimide compound with substituents R1 and R2]

wherein the R1 or R2 is one selected from a group consisting of hydrogen, halogen, unsubstituted or substituted alkyl, and unsubstituted or substituted aryl independently.

2. The dye according to claim 1, wherein, the R1 or R2 is one selected from a group consisting of halogen, tert-butyl, and carboxylate independently.

3. The dye according to claim 1, wherein the dye absorbs 400 nm~500 nm of wavelength range.

4. The dye according to claim 1, wherein the dye is a color compensating dye for a green dye.

5. A dye comprising a compound of Formula (2):

[Structure of Formula (2) showing a quinoline-naphthalenedione-naphthalimide compound with substituents R3 and R4]

wherein the R3 or R4 is one selected from a group consisting of hydrogen, halogen, unsubstituted or substituted alkyl, and unsubstituted or substituted aryl independently.

6. The dye according to claim 5, wherein the R3 or R4 is one selected from a group consisting of halogen, tert-butyl, and carboxylate independently.

7. The dye according to claim 5, wherein the dye absorbs 400 nm~500 nm of wavelength range.

8. The dye according to claim 5, wherein the dye is a color compensating dye for a green dye.

9. A dye dispersion comprising the dye according to claim 1.

10. A coloring composition comprising the dye dispersion according to claim 9.

11. A color filter comprising the coloring composition according to claim 10.

12. A dye dispersion comprising the dye according to claim 5.

13. A coloring composition comprising the dye dispersion according to claim 12.

14. A color filter comprising the coloring composition according to claim 13.

15. A method of preparing the dye, comprising:
(a) forming 8-aminoquinaldine by reducing 8-nitroquinaldine;
(b) forming an intermediate by adding at least one chemical selected from a group consisting of

[Structures of phthalic anhydride, naphthalic anhydride, 4-tert-butylphthalic anhydride, and ethoxycarbonyl phthalic anhydride]

to the 8-aminoquinaldine; and
(c) forming a dye by further adding at least one chemical selected from a group consisting of

[Structures of phthalic anhydride, naphthalic anhydride, 4-tert-butylphthalic anhydride, and ethoxycarbonyl phthalic anhydride]

to the intermediate.

16. The method according to claim 15, wherein the method further comprises (d) halogenation after the (c).

* * * * *